US011957447B2

(12) United States Patent
Tatavarti et al.

(10) Patent No.: US 11,957,447 B2
(45) Date of Patent: Apr. 16, 2024

(54) SYSTEMS AND METHODS OF USE THEREOF FOR DETERMINING AEROSOL PARTICLE CHARACTERISTICS

(71) Applicant: University of Georgia Research Foundation, Inc., Athens, GA (US)

(72) Inventors: Venkata Sreerama Narasimha Rao Tatavarti, Visakhapatnam (IN); Ramana Murthy Pidaparti, Watkinsville, GA (US); Sanjay Sarma Oruganti Venkata, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 746 days.

(21) Appl. No.: 16/905,480

(22) Filed: Jun. 18, 2020

(65) Prior Publication Data

US 2020/0397341 A1 Dec. 24, 2020

Related U.S. Application Data

(60) Provisional application No. 62/863,013, filed on Jun. 18, 2019.

(51) Int. Cl.
*A61B 6/08* (2006.01)
*A61B 5/00* (2006.01)
(Continued)

(52) U.S. Cl.
CPC ............ *A61B 5/082* (2013.01); *A61B 5/0022* (2013.01); *A61B 5/0059* (2013.01);
(Continued)

(58) Field of Classification Search
CPC ..... A61B 5/082; A61B 5/0022; A61B 5/0059; A61B 5/0803; A61B 5/4848;
(Continued)

(56) References Cited

U.S. PATENT DOCUMENTS 7,230,698 B2 * 6/2007 Kurozumi ............. G01N 15/02 356/336
8,531,663 B1 9/2013 Tochino
(Continued)

FOREIGN PATENT DOCUMENTS

ES 2311317 A1 * 2/2009 ............. G01F 23/22

OTHER PUBLICATIONS

Stelson, AW. "Theoretical and Experimental Evidence for Artifact Particulate Matter Formation in Electrical Aerosol Anlyzers." Environmental Science and Technology 23.1: 125-128. (1989) (Year: 1989).*

(Continued)

*Primary Examiner* — Linh Giang Le
(74) *Attorney, Agent, or Firm* — PABST PATENT GROUP LLP

(57) ABSTRACT

Systems and devices for detecting and characterizing stratified fluid and/or aerosol particles and droplets, and methods of use thereof to, for example, diagnose and prognose respiratory diseases and disorders are provided. The systems typically include optoelectronic sensors for detecting foreign particles like bacteria and pollutants in the air (i.e., the aerosol) based on light scattering. Information collected in this way can be used to, for example, detect or identify respiratory maladies and determine the effectiveness of methods of treatment thereof.

22 Claims, 11 Drawing Sheets

(51) Int. Cl.
*A61B 5/08* (2006.01)
*G16H 10/60* (2018.01)

(52) U.S. Cl.
CPC .......... *A61B 5/0803* (2013.01); *A61B 5/4848* (2013.01); *G16H 10/60* (2018.01); *A61B 2560/04* (2013.01)

(58) Field of Classification Search
CPC .... A61B 2560/04; G16H 10/60; G16H 40/63; G16H 50/20
See application file for complete search history.

(56) References Cited

U.S. PATENT DOCUMENTS

| | | | | |
|---|---|---|---|---|
| 8,599,378 | B2 * | 12/2013 | Merchez | G01N 15/147 356/335 |
| 9,243,892 | B2 | 1/2016 | Tochino | |
| 2010/0029763 | A1 | 2/2010 | Suarez | |
| 2018/0238776 | A1 * | 8/2018 | Karancsi | H01J 49/0027 |

OTHER PUBLICATIONS

"A Better Way to diagnose Pneumonia", [online] Georgia Tech New Center, [retrieved Oct. 2, 2020]. 2 pages Retrieved from the Internet: < https://www.news.gatech.edu/2011/02/01/better-way-diagnose-pneumonia>.
Allers, et al., "Measurement of exhaled volatile organic compounds from patients with chronic obstructive pulmonary disease (COPD) using closed gas loop GC-IMS and GC-APCI-MS", J. Breath Res., 10:026004 (2016).
Amal, et al., "Detection of precancerous gastric lesions and gastric cancer through exhaled breath", Gut, 65:400-407 (2016a).
Amal, et al., "Breath testing as potential colorectal cancer screening tool", Int. J. Cancer, 138:229-236 (2016b).
Amal, "Assessment of ovarian cancer conditions from exhaled breath", Int. J. Cancer, 136:E614-E622 (2015).
Amann, et al., "Lung cancer biomarkers in exhaled breath", Expert Rev. Mol. Diagn., 11:207-217 (2011).
Amann, et al., "Assessment of the exhalation kinetics of volatile cancer biomarkers based on their physicochemical properties", J. Breath Res., 8:016003 (2014).
Bake, et al., "Exhaled particles and small airways", Respiratory research, 20(8):1-14 (2019).
Barash, et al., "Classification of lung cancer histology by gold nanoparticle sensors", Nanomedicine, 8:580-589 (2012).
Barash, et al., "Differentiation between genetic mutations of breast cancer by breath volatolomics", Oncotarget, 6(42):44864-44876 (2015).
Baumbach, et al., "Significant different volatile biomarker during bronchoscopic ion mobility spectrometry investigation of patients suffering lung carcinoma", Int. J. Ion Mobility Spectrom., 14:159-166 (2011).
Bean, et al., "Breathprints of model murine bacterial lung infections are linked with immune response", Eur. Respir. J., 45:181-190 (2015).
Beasley, et al., "Lung microbiology and exacerbations in COPD", International Journal of COPD, 7:555-569 (2012).
Bennett, "Pediatric Pneumonia", Medscape, <http://emedicine. medscape. com/article/967822-medication> (accessed 2018).
Bhunia, et al., "Bacterial Rapid Detection using Optical Scattering Technology (BARDOT), an interdisciplinary approach", 52 pages, Nov. 3, 2010.
Bos, et al., "Exhaled breath metabolomics as a noninvasive diagnostic tool for acute respiratory distress syndrome", Eur. Respir. J., 44:188-197 (2014).
Carroll, "Laboratory Diagnosis of Lower Respiratory Tract Infections: Controversy and Conundrums", J. Clinial Microb., 40(9):3115-3120 (2002).
CHARM respiratory monitor by Philips to detect Child Pneumonia-Maternova Inc. [online-retrieved Oct. 2, 2020]. 5 pages Retrieved from the internet <https://maternova.net/products/charm-monitor-to-detect-child-pneumonia>.
Cohen-Kaminsky, et al., "A Proof of Concept for the Detection and Classification of Pulmonary Arterial Hypertension through Breath Analysis with a Sensor Array", Am. J. Respir. Crit. Care Med., 188:756-759 (2013).
Davies, et al., "Unique volatolomic signatures of TP53 and KRAS in lung cells", Br. J. Cancer, 111:1213-1221 (2014).
"Detecting Pneumonia quickly and cheaply", [online] Nanonextnl, [retrieved Oct. 2, 2020], 4 pages retrieved from the internet <https://www.nanonextnl.nl/highlights/detecting-pneumonia-quickly-and-cheaply/ >.
Fabian, et al., "Origin of Exhaled Breath Particles from Healthy and Human Rhinovirus-Infected Subjects", Journal of Aerosol Medicine and Pulmonary Drug Delivery, 24(3):137-147 (2011).
Haick, et al., "Assessment, origin, and implementation of breath volatile cancer markers", Chem. Soc. Rev., 43:1423-1449 (2014).
Hakim, et al., "Diagnosis of head-and-neck cancer from exhaled breath", Br. J. Cancer, 104:1649-1655 (2011).
Kim, et al., "Rapid detection of Mycoplasma pneumonia in a microfluidic device using immunoagglutination assay and static light scattering", Electrophoresis, 30(18):3206-3211 (2009).
Mansoor, et al., "Analysis of Volatile Compounds in Exhaled Breath Condensate in Patients with Severe Pulmonary Arterial Hypertension", PLoS One, 9:e95331 (2014).
Muir, "Distribution of aerosol particles in exhaled air", Journal of Applied Physiology, 23(2):210-214 (1967).
Nakhleh, et al., "Diagnosis and Classification of 17 Diseases from 1404 Subjects via Pattern Analysis of Exhaled Molecules", ACS Nano, 11:112-125 (2017).
Oelsner, et al., "Classifying Chronic Lower Respiratory Disease Events in Epidemiologic Cohort Studies", Annals of the American Thoracic Society, 13(7):1057-1066 (2016).
Peled, et al., "Non-invasive Breath Analysis of Pulmonary Nodules", J. Thorac. Oncol. 7:1528-1533 (2012).
Peng, et al., "Detection of lung, breast, colorectal, and prostate cancers from exhaled breath using a single array of nanosensors", Br. J. Cancer, 103: 542-551 (2010).
Peng, et al., "Diagnosing lung cancer in exhaled breath using gold nanoparticles", Nat. Nanotechnol., 4:669-673 (2009).
Phillips, et al., "Volatile organic compounds in breath as markers of lung cancer: a cross-sectional study", Lancet, 353:1930-1933 (1999).
Phillips, et al., "Breath biomarkers of active pulmonary tuberculosis", Tuberculosis, 90:145-151 (2010).
Phillips, "Point-of-care breath test for biomarkers of active pulmonary tuberculosis", Tuberculosis, 92:314-320 (2012).
Pu, et al., "Rapid broad spectrum bacterial detection using electromagnetic cellular polarization and optical scattering," 2006 Conference on Lasers and Electro-Optics and 2006 Quantum Electronics and Laser Science Conference, Long Beach, CA, 2006, pp. 1-2, doi: 10.1109/CLEO.2006.4628253.
Rabanni, "Lung-Probe: Helping to Detect Pneumonia in Infants and Babies", [online-retrieved Oct. 2, 2020]. 4 pages retrieved Oct. 2, 2020 from the Internet: < https://contest.techbriefs.com/2016/entries/medical/7185 10/ >.
"Respiratory disease diagnosis using only the sound of a patient's cough", [online] Res. App. Health, [retrieved on Oct. 2, 2020]. 6 pages Retrieved from the Internet: < https://www.resapphealth.com.au/technology/ >.
Rao, et al., "Tabla: A Proof-of-Concept Auscultatory Percussion Device for Low-Cost Pneumonia Detection", Sensors, 18(2689):1-12 (2018).
Rao, et al., "Tabla: Pneumonia Detection Device" [Retrieved online Oct. 2, 2020]. 1 Page retrieved from the Internet: < https://bigideascontest.org/projects/tabla-pneumonia-detection-device-uc-berkeley-uc-san-francisco/ >.
Robinson, et al., "Using Scattering to Identify Bacterial Pathogens", OPN Optics & Photonics News, 22(10):20-27 (2011).
Smith, et al., "Breath concentration of acetic acid vapour is elevated in patients with cystic fibrosis" J. Breath Res., 10:021002 (2016).

(56) References Cited

OTHER PUBLICATIONS

Tatavarti, et al., "Seeing the Light—Catching the Wind Technological Advances in Optical Air Data Systems," in International Conference on Communications, Networking and Signal Processing, 3-7 (2013). Abstract.
Wan, "Particle Size Concentration Distribution and Influences on Exhaled Breath Particles in Mechanically Ventilated Patients", PloS one 9(1):e87088 (2014).
Xu, et al., "Molecular and Microscopic Analysis of Bacteria and Viruses in Exhaled Breath Collected Using a Simple Impaction and Condensing Method", PloS one 7(7):e41137 (2012).
Zhang, et al., "Identification of Volatile Biomarkers of Gastric Cancer Cells and Ultrasensitive Electrochemical Detection based on Sensing Interface of Au—Ag Alloy coated MWCNTs", Theranostics, 4:154-162 (2014). better.
Waseem, "Pediatric Pneumonia Medication," Medscape, <http://emedicine. medscape. com/article/967822-medication> (accessed Apr. 18, 2022).

* cited by examiner

SYSTEMS AND METHODS OF USE THEREOF FOR DETERMINING AEROSOL PARTICLE CHARACTERISTICS

CROSS-REFERENCE TO RELATED APPLICATION

This application claims the benefit of and priority to U.S. Ser. No. 62/863,013 filed Jun. 18, 2019, and which is incorporated by reference in its entirety.

STATEMENT REGARDING FEDERALLY SPONSORED RESEARCH

This invention was made with government support under grant numbers GM104528 and HHSN272201400008C awarded by the NIH and 1150042 and 1659525 awarded by the NSF. The Government has certain rights in the invention.

FIELD OF THE INVENTION

The field of the invention generally relates to devices, systems, and methods of determining the size and other attributes of particles and droplets in an aerosol, and use thereof for diagnosing, prognosing, and treating respiratory diseases and disorders.

BACKGROUND OF THE INVENTION

Pneumonia is the single largest infectious disease causing mortality in post neonatal children. According to a World Health Organization report for the year 2017, pneumonia and other respiratory infections caused about 653,000 post neonatal (1-59 months) deaths and the disease is wide spread in developing and under developed countries especially in South Asian and Sub-Saharan regions (World Health Organization, "Causes of Child Mortality", (2017)). According to an analysis by Johns Hopkins, pneumonia is on course to kill about 11 million children by 2030 worldwide (Janati, Save the Children, "Pneumonia to Kill Nearly 11 Million Children by 2030," (2018)). In the US about 51,459 deaths were reported in the year 2016 due to pneumonia and influenza in both adults and children, of which 1423, were from the state of Georgia (Centers for Disease Control and Prevention, National Center for Health Statistics, Influenza/Pneumonia Mortality by State 2017, (updated 2019)). Further, 154,444 deaths were reported throughout the US due to chronic lower respiratory diseases and 4805 deaths were from the state of Georgia alone (Centers for Disease Control and Prevention, National Center for Health Statistics, Chronic Lower Respiratory Disease Mortality by State 2017, (updated 2019)).

A significant number of deaths can be averted through timely diagnostics and vaccination for prevention. Diagnosis of these lung related diseases begins with physical observation, blood serum examination, chest X-rays, pulse oximetry tests, auscultation, followed by CT scans and pleural fluid cultures in chronic cases (Carroll, J. Clinial Microb., 40(9):3115-3120 (2002), DOI:10.1128/JCM.40.9.3115-3120.2002; Oelsner, et al., *Annals of the American Thoracic Society,* 13(7): 1057-1066 (2016). DOI: 10.1513/AnnalsATS 0.201601-0630C). In all these procedures, it is important to diagnose the disease accurately and quickly, and to consider it when selecting a treatment course from a wide variety available. Currently, the only pathogen-detecting method in use is growing cultures in vitro, and many factors render this technique slow and in effective due to laboratory complications and limitations (Bennett, Medscape, "Pediatric Pneumonia," (2018)).

In view of these shortcomings, improved tools and techniques are needed.

Thus, it is an object of the invention to provide improved systems, devices, and methods of use thereof for determining the size and other attributes of particles and droplets in an aerosol.

It is another object of the invention to use recorded and deduced attributes of particles and droplets in an aerosol for diagnosing, prognosing, and treating respiratory diseases and disorders.

SUMMARY OF THE INVENTION

Systems and devices for detecting and characterizing stratified fluid and/or aerosol(s) thereof and/or particles and droplets thereof, and methods of use thereof to, for example, to diagnose and prognose respiratory diseases and disorders are provided. The systems typically include optoelectronic sensors for detecting foreign particles like bacteria and pollutants in the air (i.e., the aerosol) based on light scattering. Information collected in this way can be used to detect or identify respiratory maladies. For example, the systems and methods can be used to detect a lung infection through pathogen density in a subject's breath.

The disclosed systems typically include a light irradiation part, a photo detector (PD) part, and a data acquisition (DAQ) part. The irradiation part and the PD part are positioned at an appropriate distance apart for a stratified fluid or an aerosol to be passed between them, undisturbed. The characteristics of scattered light can be detected by an active sensing area of the PD part and converted to an electrical signal. The electrical signal can in-turn be converted to digital data by the DAQ part. The alignment angle between light irradiated from the light irradiation part and the active sensing area of the PD part is typically chosen to result in forward/backward scattering of light due to anthropogenic aerosols, and is typically about 180 degrees or is 180 degrees.

In preferred embodiments, the light irradiating part is a laser. The light can be an un-collimated, un-processed raw point laser light beam.

The PD part includes an active sensing area that can detect light from the light irradiating part. The active sensing area of the PD part can include, for example, one or more photodiodes. In some embodiments, the system includes one or more amplifiers that can amplify the electrical signal. The amplifier(s) can be part of the PD part, or a separate part in the system.

The DAQ part can include an integrated circuit that facilitates linkage between the DAQ part and a computer. The computer can be a remote computer. The linkage can be wired or wireless.

In some embodiments, the system further includes one or more voltage regulators and a power supply.

The system can include, or be otherwise operably linked, to a computing environment, most typically a computer. Exemplary computers include, but are not limited to, supercomputers, mainframe computers, minicomputers, microcomputers such as desktop computers, and mobile computers such as laptops, netbooks, tablets, cellphones and smartphones.

One or more parts of the systems can be partially or complete contained or enclosed within one or more housings. For example, in some embodiments, the system contains or encloses a portion of, or all of, the light irradiation part, the PD part, the DAQ part, the voltage regulator, the power supply, or any combination thereof. In some embodiments, the computing environment, (i.e., the computer) is not contained or enclosed in the housing. Thus, the computing environment can be physically separate from other parts of the system. For example, in some embodiments, the system part or parts contained within the housing are in wireless communication with the computer, e.g., via the DAQ part.

Exemplary housings arc also provided. For example, in some embodiments, a portion or all of the light irradiation part, the PD part, the DAQ part, the voltage regulator, the power supply, or any combination thereof, are contained or enclosed in one or more compartments in the housing. The housing can be compact, portable and lightweight, made of a suitable material compatible with medical standards for human usage. The housing can include one or more inlets and/or outlets to facilitate delivery of the aerosol into and/or through the housing. The housing can include one or more channels or compartments for wires or connectors electrically connecting one or more of the parts of the system. The housing can be formed of a plastic, paper, composite, or other permanent or disposable material. The housing can be handheld.

Devices including one or more system parts housed within a housing are also provided. For example, in some embodiments, the device includes a light irradiation part, a PD part, a DAQ part, a voltage regulator, a power supply, or any combination thereof partially or completely contained or enclosed in the housing. Typically, the device does not include a computer, but preferably can be, or is, in wired or wireless communication therewith.

In some embodiments, the system, housing, or device further includes a stratified fluid and/or aerosol. The stratified fluid or aerosol can be delivered to the system by a subject breathing or coughing directly or indirectly into a space or compartment between the light irradiating part and the PD part, or artificially using, for example, a nebulizer or humidifier.

Methods of use are also provided. For example, a method of characterizing the particles and/or droplets of a stratified fluid and/or aerosol can include passing an effective amount of the aerosol through light irradiated by the light irradiation part of a disclosed system or device for the PD part to detect light scattered by the stratified fluid and/or aerosol and generate an electrical signal corresponding to the scattered light physical characteristics, for example the scattered light's x and y positions and intensity. The method can include converting the electrical signal to digital data. The method can include recording, collecting and/or processing the digital data by the system, on a computer linked thereto, or a combination thereof. The method can include repeating the detecting, generating, converting, and optionally the recording, collecting and/or processing one or more times, preferably at a fixed time interval.

The processing can include using the digital data to determine the deflection magnitude, the deflection direction and/or the deflection frequency of the light; the size, sizes, or size range, or density or rate of particles and/or droplets in the aerosol; or any combination thereof. Such information can be referred to as deduced data determined by applying mathematical formulae to the digital data collected by the system (also referred to as recorded data).

In some embodiments, a stratified fluid includes two or more aerosols. The methods can be used to characterize one or more of the aerosols. In some embodiments, an aerosol includes particles and/or droplets of known content, unknown content, or a mixture thereof.

The passing of the stratified fluid or aerosol into or through the system or device can include, for example, a subject breathing and/or coughing into the system. In some embodiments, the subject has or is suspected of having a respiratory disease or disorder. Preferred diseases and disorders include, but are not limited to, asthma (e.g., adult-onset asthma, allergic asthma, asthma, chronic obstructive pulmonary disease (COPD) overlap, exercise-induced bronchoconstriction (EIB), non-allergic asthma, or occupational asthma); infections such as pneumonia; and chronic obstructive pulmonary disease (COPD), or a symptom or disorder associated therewith such as emphysema, chronic bronchitis, and refractory (non-reversible) asthma.

A stratified fluid and/or aerosol profile or collection of profiles including any recorded or deduced data such as the x and/or y position, the power, the deflection magnitude, the deflection direction, and/or the deflection frequency of the scattered light; the size, sizes, or size range, or density or rate or speed of particles and/or droplets in the aerosol; or any combination thereof can be prepared.

Methods of using the data recorded or deduced using the disclosed systems, devices, and methods are also provided. For example, a method of diagnosing and/or prognosing a respiratory disease or disorder can include comparing one or more of a subject's aerosol profile(s) with one or more disease or disorder stratified fluid and/or aerosol profiles, and diagnosing the subject as having a disease or disorder or when part or all of the subject's profile or profiles match the corresponding disease or disorder's profile(s). The subject's profile(s) can also be compared to profiles of subjects with the same or similar disease or disorder and having a known outcome to prognose the subject's likely outcome. In some embodiments, the systems, devices, and methods can estimate the occurrence of an upcoming respiratory event, such as an asthma attack.

In another example, the effectiveness of a treatment can be determined by comparing first and second profiles of a subject with a disease or disorder to a healthy profile or profiles, wherein the first and second profiles are prepared before and after at least one treatment for the disease or disorder respectively, and wherein the treatment is determined to be effective if the subject's second profile is more similar to the healthy profile than the first profile.

DETAILED DESCRIPTION OF THE INVENTION

I. Definitions

Figure 1:
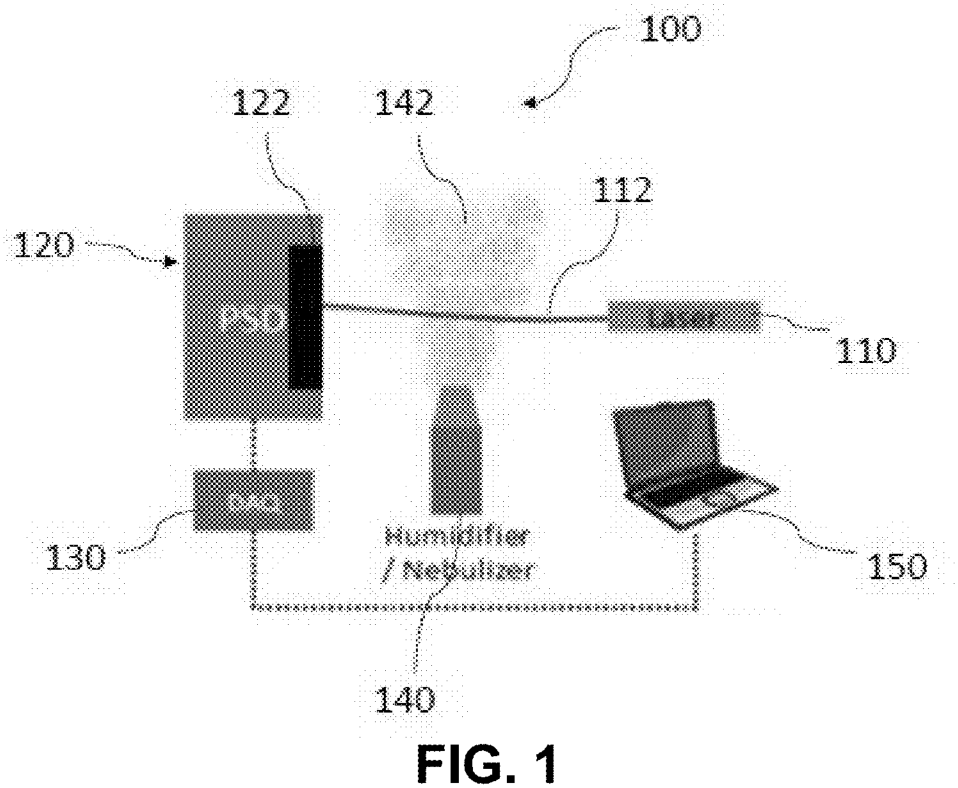
FIG. 1 is an illustration depicting an exemplary system of the disclosure.

As used herein, the term "stratified fluid" means a fluid in which one or all the physical characteristics of the fluid is/are a function of space, i.e., the physical characteristic(s) of the fluid can be categorized into different strata.

As used herein, the term "aerosol" means a suspension of fine solid particles or liquid droplets, in a stratified fluid.

As used herein, the term "data acquisition (DAQ)" is the process of measuring an electrical or physical phenomenon such as voltage, current, temperature, pressure, or sound.

As used herein, the term "observation angle" or "angle of observation" is the angle formed by a light beam, such as the light irradiated from a laser, and a detector.

II. Systems for Measuring Optical Scattering of Particles in Aerosols

Exhaled breath involves expulsion of air from the lungs laden with aerosols whose composition is dictated by biological processes. Such aerosols can be used as biomarkers of health/disease. Typically, a stratified fluid has one or more aerosols therein. Each aerosol can include one or more species of particles and/or droplets. Thus, the presence or absence of certain aerosols or particles and/or droplets therein in the cough or breathe of a subject can be an indication that the subject has a disease or disorder characterized by the aerosol(s).

Systems and devices for monitoring such stratified fluids and aerosols thereof, and methods of use thereof for, e.g., indicating the health of the individual arc provided. Exemplary applications include diagnosing respiratory diseases and disorders.

The systems and devices typically include a light irradiation part and photo detector (PD) and analogue-to-digital circuitry. Upon illumination, light emitted from the light irradiation part propagates through the stratified fluid (air/gas/liquid) whose characteristics are to be monitored. The light irradiation part can be a laser diode. The light can be free from collimation and/or other processing when it is propagated through the stratified fluids. Thus, in some embodiments, the light emitted from the light irradiation part is an un-collimated, un-processed raw laser beam. When propagating through the stratified fluid and/or aerosol the light modulates in relation to the dynamic motions of the stratified fluid and/or aerosol, producing scattered light. The modulation or scatter pattern falling on the photo detector changes with changes in the amplitude and frequency of motions occurring in stratified fluid. The light irradiation part and the photo detector are aligned in such a way that the scatter light (e.g., modulated laser light) falls on the active sensing area of the photo detector, generating analogue output signal(s). The photo detector's output electrical signal is received as input by analogue-to-digital conversion circuitry (i.e., a data acquisition (DAQ) part)). The output digital signals can be recorded. The digital signal are typically processed and provide characteristics of the motions in the stratified fluid.

The disclosed systems and devices can be used to detect various types of aerosols occurring in the surrounding fluid and monitor them in real time.

The systems can also include one or more amplifiers, voltage regulators, and power supplies, and can be linked to a computer, including mobile devices, by wired or wireless connection. The computer can process the data collected by the system, which can be used to determine the characteristics of particles and droplets in the aerosol sample and create a profile for the aerosol sample. Methods of using an aerosol sample profile, for example, to determine the content(s) of the aerosol, and optionally diagnose a subject as having a disease or condition associated with the identified contents or a particular profile associated therewith are also provided.

A. Irradiation Part

The light irradiation part typically includes a laser suitable to irradiate a region through which an aerosol sample or stratified fluid can be passed or is passing. Any suitable light source can be used. The light irradiation part is most typically a spatially and temporally coherent light beam of smaller cross-sectional beam diameter of an effective intensity and wavelength, for example any laser, that can be scattered by an aerosol and detected as scattered light on a PD. In preferred embodiments, the light irradiation part is a low power diode laser operating in the visible region of the spectrum. In specific embodiments, the laser is a 670 nm (red) diode (semiconductor) laser. The laser can have, for example, a 5 mW power output, though other suitable sources are known in the art. For example, the laser may have a different power, intensity, frequency, wavelength, light beam diameter, etc.

The light irradiation part can also, but need not necessarily include, a laser light guide mechanism that focuses the irradiated light in a region through which the fluid and/or aerosol sample is passed. The laser light guide mechanism can include, for example, a light focusing/converging len(s) or the like. In some embodiments, the system includes a collimation part, such as a pinhole, that narrows the laser beam. The collimation part can be a feature of the light irradiation part or a separate part. In some embodiments, the system is free of a collimation part. Thus, in some embodiments the light is un-collimated light.

B. Photo Detector Part

Light from the light irradiating part scatters based on the specific contents of the environment through which light propagates, and characteristics of the scattered light are measured, thus making it possible to determine the aerosol features which are responsible for the scattering of light. As discussed in more detail below, the size of the particles and droplets can be deduced by using the PD to detect changes in beam position and power caused by the particles and droplets on its active sensing area.

Examples of scattered light characteristics that can be measured include, the scattered light intensity vis-a-vis the location of the source of light, the position of the scattered light on the detector(s). Typically, the measured scattered light characteristics involve measurement of scattered light falling on the detector after aligning it to be directly facing the source of light.

The light characteristics that need to be measured can be determined based on the applications envisaged herein. Thus, a practitioner may measure one or all characteristics generally known to those in the field of photonics.

The photo detectors can be, for example, a standard solid-state silicon photo detector. In specific embodiments, the photo detector has a circular active sensing diameter of 10 mm, with a BNC (Bayonet Neill—Concelman) connector for providing output electrical signal. The angle of observation between the light irradiation part and the photo detector is about 180° or is 180°.

In general, the specific choice of the light source as well as the PD can be made based on engineering design considerations for specific applications.

The system can also include an amplifier part that increases the electrical current output from the photodiode. The amplifier part can be a feature of, or separate from, the PD. The PD used in the examples below is QP50-6SD2, though PD of different types, sizes, sensitivities and resolutions can also be used.

C. Data Acquisition Part

The system includes analogue data acquisition and processing circuitry, also referred to herein as a data acquisition (DAQ) part. The DAQ part is typically connected to the output of the photo detector. In preferred embodiments, the DAQ part is a DAQ device, such as a Data Acquisition Card.

The DAQ part typically acts as the interface between the PD and a computer or a computing device. In some embodiments, the DAQ part digitizes incoming analog signals so that a computer can interpret them.

The DAQ part can include one or more of a signal conditioning circuitry, analog-to-digital converter (ADC), and computer bus.

Signal conditioning circuitry manipulates a signal into a form that is suitable for input into an ADC. This circuitry can include amplification, attenuation, filtering, and isolation. Some DAQ devices include built-in signal conditioning designed for measuring specific types of sensors.

Analog signals from sensors are typically converted into digital before they are manipulated by digital equipment such as a computer. An ADC is a chip that provides a digital representation of an analog signal at an instant in time. In practice, analog signals continuously vary over time and an ADC takes periodic "samples" of the signal at a predefined rate. These samples are transferred to a computer over a computer bus where the original signal is reconstructed from the samples in software.

The computer bus serves as the communication interface between the DAQ device and computer for passing instructions and measured data. The data acquisition part can connect to a computer through a wired or wireless connection. DAQ devices are commercially available with most common computer buses including, slots and ports for connect via USB, PCI, PCI Express, Ethernet, wireless options such as 802.11 Wi-Fi and Bluetooth, and data storage devices such as an SD card.

The data acquisition part can also include other functions for automating measurement systems and processes, for example, digital-to-analog converters (DACs) for output analog signals, digital I/O lines for input and output digital signals, and counter/timers to count and generate digital pulses.

Any suitable commercially available DAQ device can be used. The DAQ part utilized in the examples below is Arduino UNO.

D. Voltage Regulators, Power Supplies, and Batteries

The system can also include one or more voltage regulators to maintain a constant voltage level to one or more parts of the system. For example, in preferred embodiments, a voltage regulator ensures delivery of a constant voltage level from a power supplies to the optical PD part.

The system can further include or be otherwise connected to one or more power supplies to power one or more parts of the system including, but not limited to, the light irradiation part, the optical PD part, and the data acquisition part. The light irradiation part, the optical PD part, and the data acquisition part can share the same or different power supplies.

The system can further include or be otherwise connected to one or more batteries to power one or more parts of the system including, but not limited to, the light irradiation part, the optical PD part, and the data acquisition part. The light irradiation part, the optical PD part, and the data acquisition part can share the same or different batteries.

Suitable power supplies and/or batteries are known in the art and can be selected to be compatible with the parts requiring power.

E. Housing

The foregoing parts can be contained in the same of different housings. Typically, the housing suitably arranges the light irradiation part and the PD part such that an aerosol or stratified fluid can be passed between them and the PD can sense the power and position of the incident beam of the light irradiation part on its active sensing area. Preferably, the housing presents the light irradiating part and PD part in a forward/back scattering configuration. Preferably the path between the laser and the PD is unobstructed by the housing itself or other parts or features housed therein. The separation distance between the light irradiation part and the PD are determined by the exact engineering considerations and applications; for example the distance between the irradiation part and PD was set to 1 inch in the examples below.

In some embodiments, the housing provides compartments for one or more of a laser, a PD, the aerosol, an amplifier, a DAQ, a voltage regulator, a power supply and/or battery.

In some embodiments, the compartment for the aerosol is open at two ends or regions, so that aerosol or stratified fluid can be directly or indirectly passed through the laser beam. In some embodiments, the housing includes one or more inlets and/or outlets. The inlet and/or outlet can be a pipe-like provision that facilitates the formation of a tight seal between a subject's lips and the housing. In some embodiments, the inlet and/or outlet includes or is suitable for connection to tubing or piping. In some embodiments the system or the housing itself includes the tubing or piping. In some embodiments, the tubing or piping is connected to a breathing mask. Thus, in some embodiments, the system or the housing itself includes a breathing mask.

The housing can also include compartments and/or channels for passage of wires that can facilitate electrical connection between the system's parts and their power supply or battery, and/or among the systems parts, so that system is operably linked within the housing.

The housing can be composed of any suitable materials or combination of materials. Such materials include, but are not limited to, plastics, paper, composites. The materials can be permanent or disposable. Part of the device can be 3D printed parts, or otherwise fabricated using any suitable means.

Figure 5A:
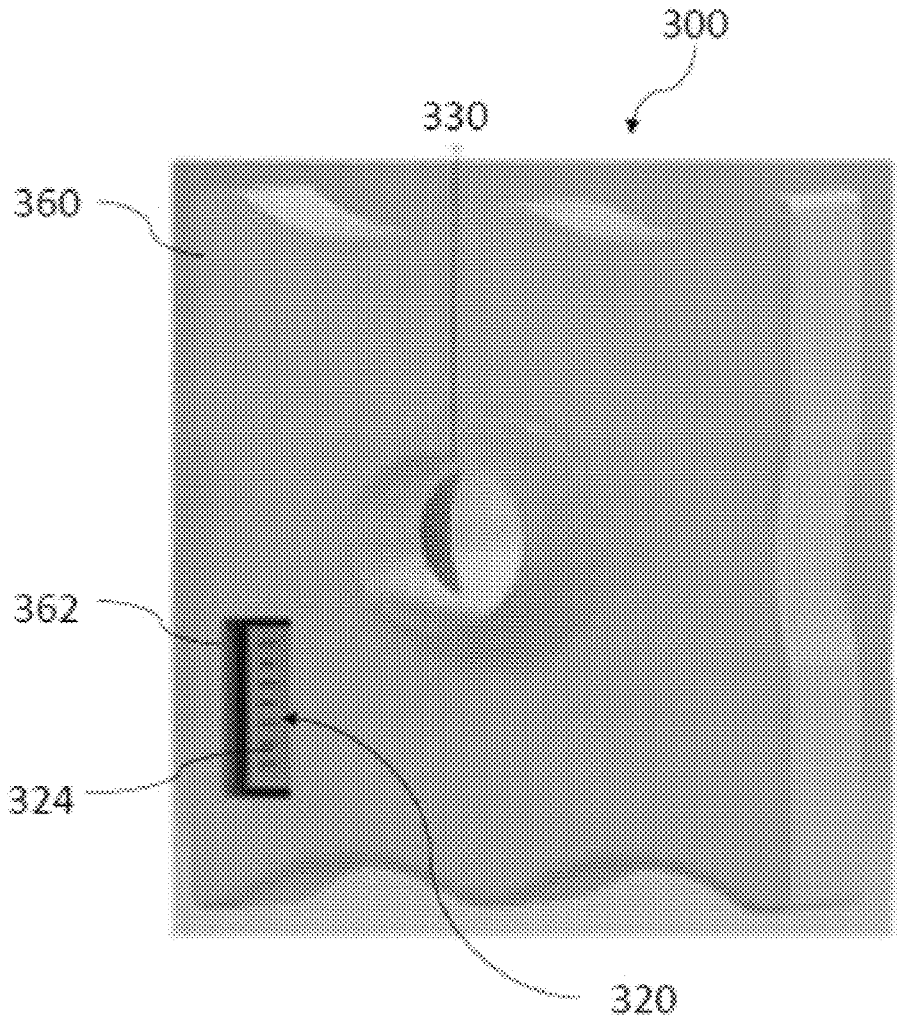
FIGS. 5A-5B are illustrations of parts of exemplary systems of the disclosure, and highlight the structure of an exemplary housing for system components.
Figure 5B:
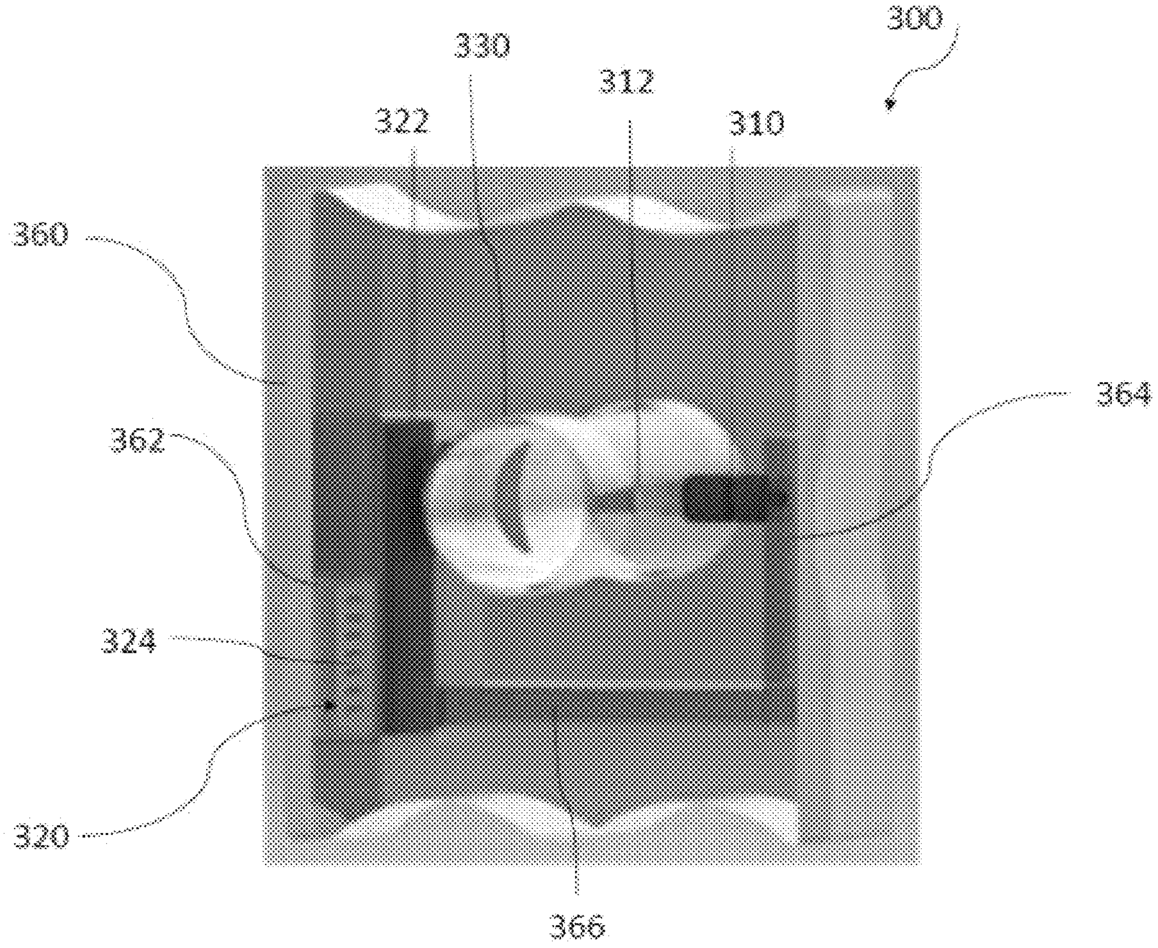
Figure 5C:
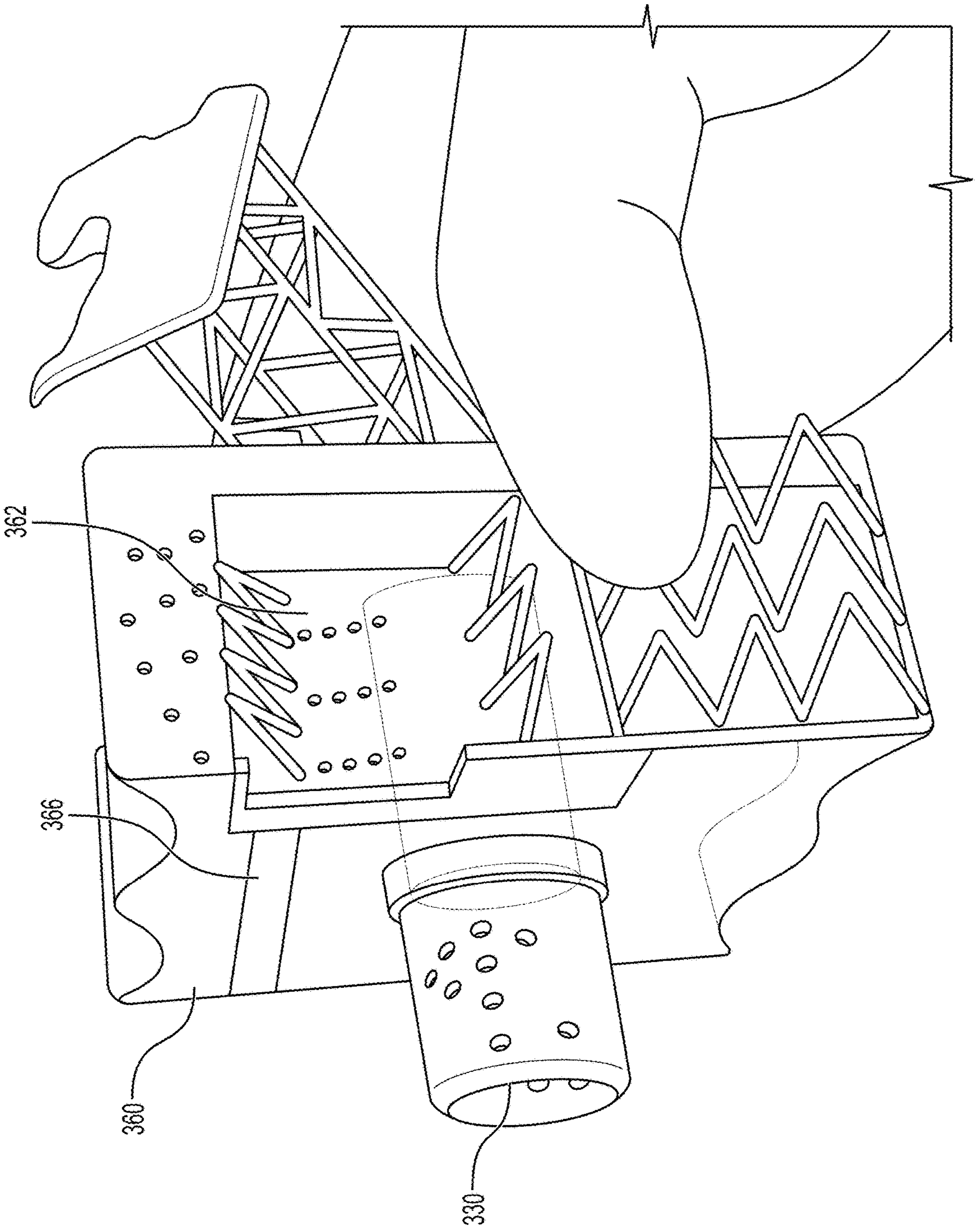
FIG. 5C is an illustration of the exemplary housing illustrated in FIGS.

Exemplary housings are depicted in FIGS. 5A-5C. FIG. 5A is an illustration of a part of a system (300) having a housing (e.g., acrylic painted black or clear or opaque resin) (360) featuring an inlet/outlet (330) for an aerosol or stratified fluid, an interior region with an opening (362) for a photo detector (PD) part, and the photo detector (PD) part (320) with a 7 pin connector (324) exposed through an opening in the housing. FIG. 5B is an illustration of a part of a system (300) having a housing (360) featuring an inlet/outlet (330) for an aerosol, an interior region with an opening (362) for a photo detector (PD) part, channels for the passage of electrical connections such as wires (364) and (366), and the photo detector (PD) part (320) including a photo sensing area having a photodiode, an amplifier circuit, and 7 pin connector (324) housed in region (322) and having the 7 pin connector (324) exposed through an opening in the housing. The part of the system (300) also includes a laser (310), a beam emitted therefrom (312) that passes through a compartment bordered by the inlet/outlet (330) to the position sensing area (e.g., a photodiode) of the photo detector (PD) part (320) optionally further including an amplifier circuit. FIG. 5C is photograph of the housing (360) illustrated in FIGS. 5A and 5B. An inlet/outlet (330) for an aerosol, an interior region with an opening (362) for a photo detector (PD) part, and channels for the passage of electrical connections such as wires (366) are visible in the photograph.

F. Computing Environment

Data collected using the disclosed system is typically transferred and analyzed with the assistance of a computer system. A computing environment can include, for example, a processing unit and memory. The processing unit executes computer-executable instructions and may be a real or a virtual processor. In a multi-processing system, multiple processing units execute computer-executable instructions to increase processing power. The memory may be volatile memory (e.g., registers, cache, RAM), non-volatile memory (e.g., ROM, EEPROM, flash memory, etc.), or some combination of the two. In some embodiments, the memory stores software implementing described techniques.

A computing environment may have additional features. For example, the computing environment can include storage, one or more input devices, one or more output devices, and one or more communication connections. An interconnection mechanism such as a bus, controller, or network can interconnect the components of the computing environment as well as other parts of the systems described above. Typically, operating system software provides an operating environment for other software executing in the computing environment, and coordinates activities of the components of the computing environment.

Storage may be removable or non-removable, and includes magnetic disks, magnetic tapes or cassettes, CD-ROMs, CD-RWs, DVDs, or any other medium that can be used to store information and can be accessed within the computing environment. In some embodiments, the storage stores instructions for the software.

Typically, the computing environment receives input directly or indirectly from a part of the disclosed system, most commonly a data acquisition part. The computing environment can also receive input from one or more additional devices. Input device(s) include, but are not limited to, touch input device such as a keyboard, mouse, pen, trackball, touch screen, or game controller, a voice input device, a scanning device, a digital camera, or another device that provides input to the computing environment. The output device(s) may be a display, printer, speaker, or another device that provides output from the computing environment.

Communication connections can enable communication over a communication medium to another computing entity. The communication medium can, for example, convey information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations may be described in the general context of computer-readable media. Computer-readable media are any available media that may be accessed within a computing environment. By way of example, and not limitation, within the computing environment, computer-readable media include memory, storage, communication media, and combinations of any of the above.

The computing environment can be, without limitation, a supercomputer, mainframe computer, minicomputer, a microcomputer such as a desktop, or a mobile computer (also referred to as a mobile device) such as a laptop, netbook, tablet, cellphone or smartphone.

In some embodiments, the computing environment is or includes a mobile device. The mobile device can receive wired or wireless input from a part of the system, typically a data acquisition part. In some embodiments, the input data is processed on software present on the mobile device or transferred from the mobile device to another computer for processing. The software can be, for example, a mobile application. The mobile application can be, for example, a native application installed and running on the device, a web application that provides online application assess through, for example, a mobile device browser, or a hybrid application that includes elements of both native and web-based applications.

Any of the computer-readable media herein can be non-transitory (e.g., volatile or nonvolatile memory, magnetic storage, optical storage, or the like).

Any of the storing actions described herein can be implemented by storing in one or more computer-readable media (e.g., computer-readable storage media or other tangible media).

Any of the things described as stored can be stored in one or more computer-readable media (e.g., computer-readable storage media or other tangible media).

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

Any of the methods described herein can be implemented by computer-executable instructions stored in one or more computer-readable storage devices (e.g., memory, magnetic storage, optical storage, or the like). Such instructions can cause a computer to perform the method.

The programs, processes, or methods described herein are not related or limited to any particular type of computing environment, unless indicated otherwise. Various types of general purpose or specialized computing environments may be used with or perform operations in accordance with the teachings described herein. Elements of the described embodiments shown in software may be implemented in hardware and vice versa.

III. Exemplary System Embodiments

FIG. 1 shows an exemplary set-up of a disclosed system (100). A humidifier/nebulizer (140) delivers an aerosol (142) into a space between a laser (110) and photo detector (PD) part (120) including an active sensing area (122). The aerosol scatters the laser beam (112) emitted by the laser (110), deflecting the beam and changing power on the active sensing area (122). The beam deflection data of the scattered laser beam are electronically acquired by a data acquisition (DAQ) part (130) further digitized for transfer to a computer (150) for analysis.

Figure 4:
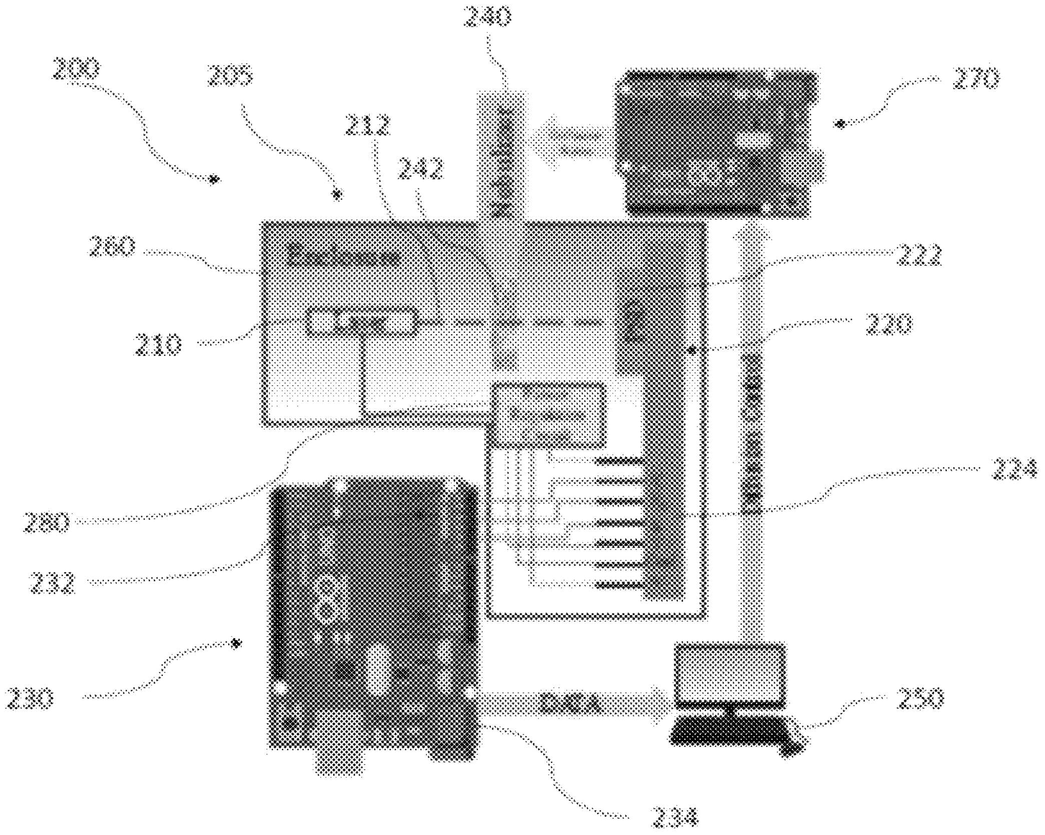
FIG. 4 is an illustration depicting an exemplary system of the disclosure.

FIG. 4 shows another exemplary set-up for a disclosed system (200). A computer (250) controls the rate delivery of aerosol particles from a nebulizer (240) through an Arduino board (270), analog outputs. The delivered aerosol (242) is passed into a space between a laser (210) and photo detector PD part (220) with a quad photo diode active sensing area (222), built-in current-to-voltage amplifiers, and electrical connector (224) connecting the PD part (220) to power and voltage regulator (280) and a data acquisition (DAQ) part. The laser irradiance part (210) also is connected to the power and voltage regulator (280). The scattering due to aerosol in the laser beam (212) emitted by the laser (210) causes change in beam position and power captured by the PD (220). The DAQ part receives the analog signal from the PD part through an analog input region (232), digitizes the analog data and the output region (234) sends it to a computer (250) for analysis. Some of these parts are enclosed in a housing (260).

Figure 5D:
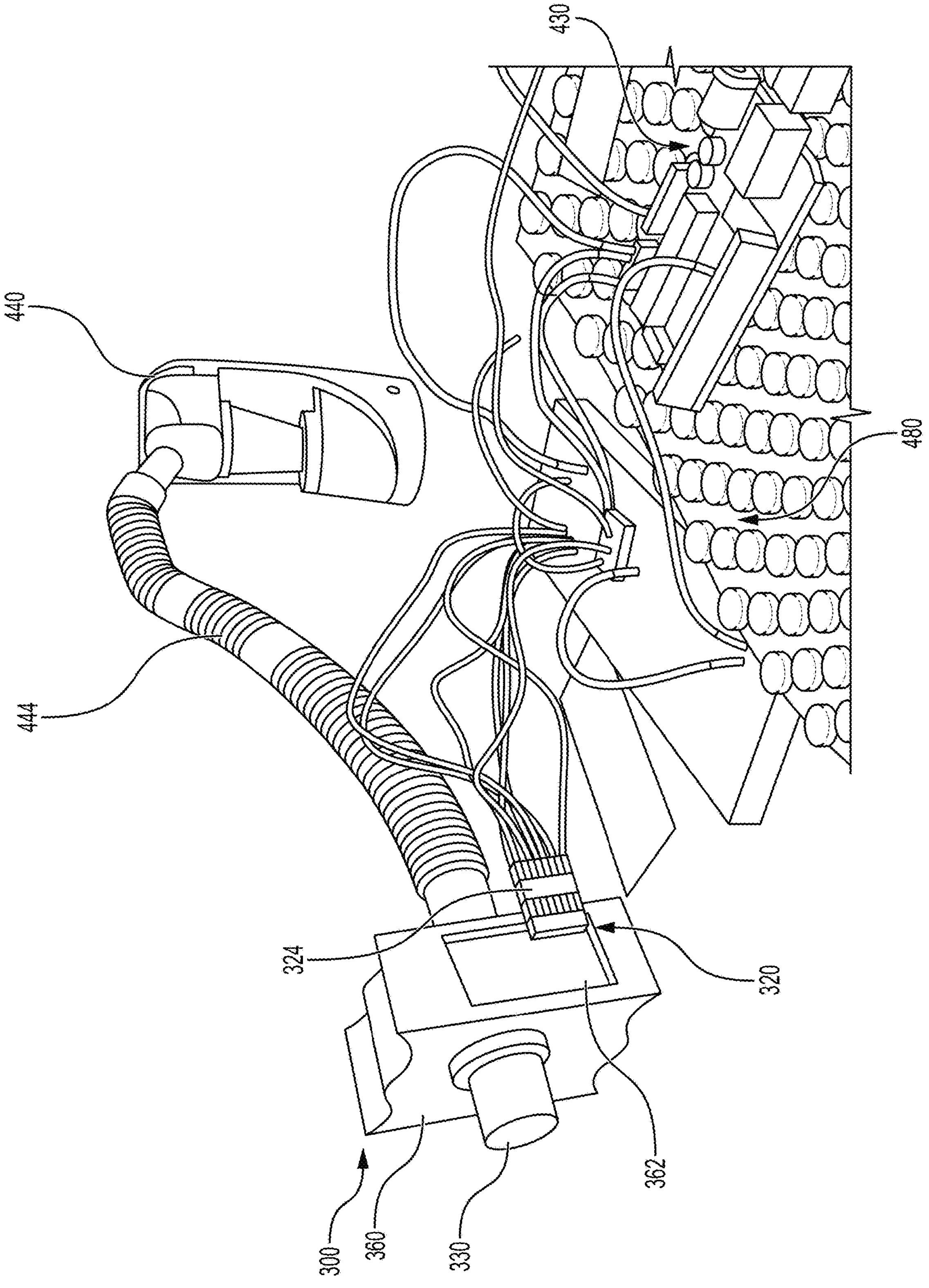
FIG. 5D is an illustration of an exemplary system of the disclosure featuring the exemplary housing of FIGS. 5A-5C.

FIG. 5D shows another exemplary set-up for a disclosed system (400). The image shows a part of the system (300) having a housing (360) featuring an inlet/outlet (330) for an aerosol, an interior region with an opening (362) for a photo detector (PD) part (320). The connector (324) of the PD part (320) is connected via wires to a power source (480) and a data acquisition (DAQ) part (430). The DAQ part (430) is also connected to the power source (480). A nebulizer (440) creates an aerosol that is delivered to the housing (360) via a tube (444) connected an inlet/outlet on the housing.

Figure 6:
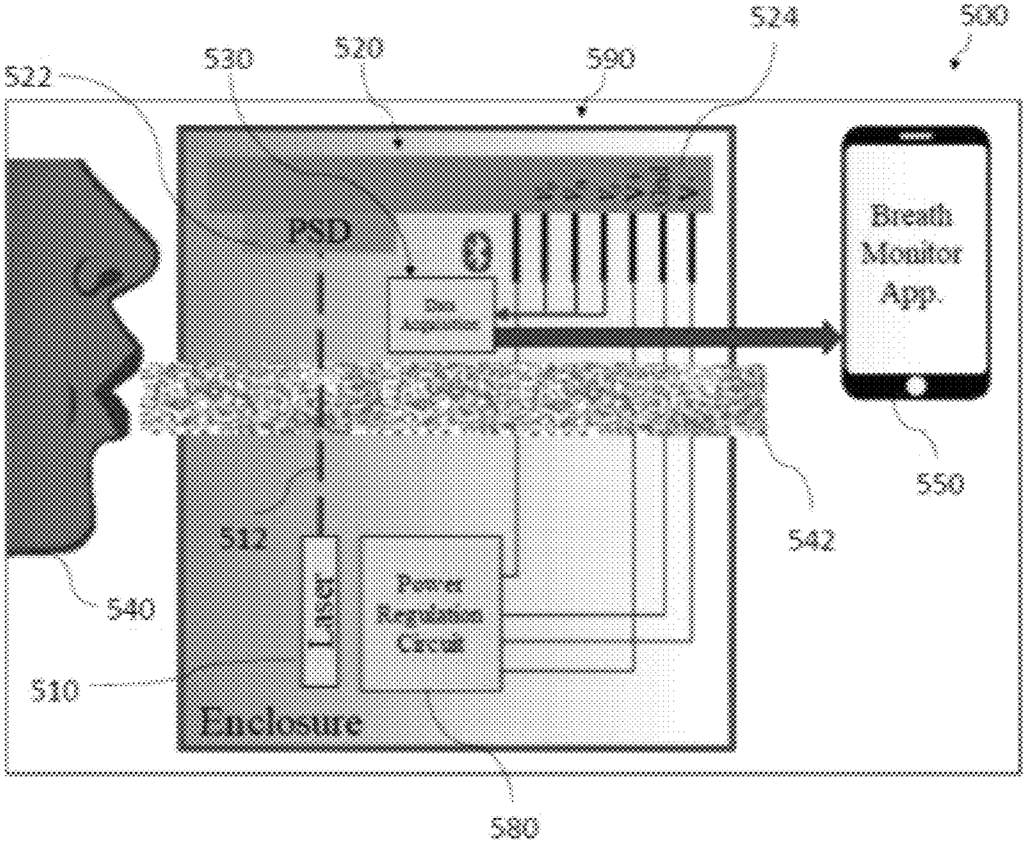
FIG. 6 is an exemplary autonomous system of the disclosure enclosed in a single housing and wirelessly connected to a mobile device running an application for analysis of data collected by the system.

FIG. 6 shows another exemplary set-up for a disclosed system (500). A PD part (520), data acquisition (DAQ) part (530), and voltage regulator and power supply (580) are enclosed within a single housing (590). A laser (510) emits a laser beam (512) across an aerosol or stratified fluid (542) delivered from a subject (540) though the housing (590). Laser light scattered by the aerosol is detected by the position sensing area (522) of the PD part (520). A connector (524) on the PD part facilitates wired connection between the PD part and the DAQ part (530) and the voltage regulator and power supply (580). The DAQ part (530) converts the analog signal delivered from the PD part (520) to a digital signal and transmits it via Bluetooth wireless connectivity to a mobile device (550) running an application that facilitates analysis and/or interpretation of the collected data.

IV. Methods of Use

A. Use of Optical Scattering to Deduce Particle Characteristics

Optical scattering is a promising mechanism for monitoring changes in stratified fluid. Most of these systems involve complex optical systems and incur huge costs in their development. Developing smaller and accurate systems for particle monitoring has a huge advantage. See, e.g., (Tatavarti, et al., "SEEING THE LIGHT— CATCHING THE WIND Technological Advances in Optical Air Data Systems," in International Conference on Communications, Networking and Signal Processing, 2013, pp. 3-7) and work on non-intrusive sensors for monitoring stratified fluids, for aircrafts and submerged bodies in the oceans.

The devices and systems can be used to detect particles in a medium through scatter. For example, x and y positions and power data can be collected by the system, and once collected the data can be processed by a computer to determine the size(s) of the particle(s) and/or droplet(s) in the aerosol. The computer can utilize a software executing a computational scheme or algorithm that facilitates such processing according to mathematical relationships such as those discussed below.

B. Scattering of Light by Air Molecules and Aerosols 1. Rayleigh Scattering Light is an electromagnetic radiation with oscillating electric and magnetic fields perpendicular to each other and perpendicular to the direction of propagation.

Mathematically, an electric field can be represented by $$E_z=E_0\cos(\omega_t) \quad \text{Eq. (1)}$$

Figure 7A:
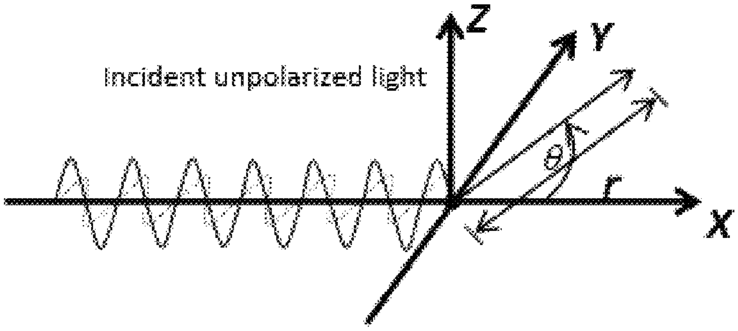
FIG. 7A is an illustration of light scattered by a particle.

See FIG. 7A.

A dipole moment is generated by the light scattered by a particle. This is induced in the particle if the particle is polarizable and is in the same direction of the incident field. This is also proportional to the intensity of the incident field given by $$p=\alpha_p E_0\cos(\omega_t) \quad \text{Eq. (2)}$$

where, p is the dipole moment, a p is the polarizability constant and c is the speed of light.

In addition, scattered light field is proportional to $$\left(\frac{1}{c^2}\right)\left\{\frac{d^2p}{dt^2}\right\} \quad \text{Eq. (3)}$$

$$\left\{\frac{d^2p}{dt^2}\right\}$$

is the acceleration of the charge on the dipole moment

Scattering varies inversely with distance and a function of angle of observation $\theta_z$ (a sin function).

The above equation can be written as $$E_s=\left(\frac{1}{r}\right)\left(\frac{1}{c^2}\right)\sin(\theta_z)\left\{\frac{d^2p}{dt^2}\right\}=-\left(\frac{1}{r}\right)\left(\frac{1}{c^2}\right)\alpha_p E_0\omega^2\sin(\theta_z)\cos(\omega t)=-\alpha_p E_0\left(\frac{4\pi^2}{r\lambda^2}\right)\sin(\theta_z)\cos\left(\frac{2\pi c}{\lambda}t\right) \quad \text{Eq. (4)}$$

where $$\lambda=\frac{2\pi c}{\omega}$$

is the wavelength

The intensity of electric field is given by $$I_s=|E_s|^2 \Rightarrow I_s=\alpha_p^2 I_{OZ}\left(\frac{16\pi^4}{r^2\lambda^4}\sin^2(\theta_z)\right) \quad \text{Eq. (5)}$$

$I_{oz}=E_0^2$ is the intensity of the z polarized incident light

For an unpolarized light in x direction, the incident intensity is given by $$I_0 = \frac{1}{2}I_{OZ} + \frac{1}{2}I_{OY} \quad \text{Eq. (6)}$$

$l_{oz}$ and $l_{oy}$ are the incident light polarized in the z and y directions respectively The scattered light intensity is given by $$I_s = \frac{1}{2}I_{sz} + \frac{1}{2}I_{sy} = \frac{I_0 8\pi^4\alpha_p^4}{r^2\lambda^4}(\sin^2\theta_z + \sin^2\theta_y) \quad \text{Eq, (7)}$$

In an inner space $\cos^2\theta_x + \cos^2\theta_y + \cos^2\theta_z = 1$ $$I_s = \frac{I_0 8\pi^4\alpha_p^4}{r^2\lambda^4}(1 + \cos^2\theta_x) \quad \text{Eq. (8)}$$

Assuming that the volume of scatter includes many particles, n moles of particles of nL particles, where L is Avogadro's number then, $$I_s = \frac{I_0 nL}{V}\left(\frac{n8\pi^4\alpha_p^4}{r^2\lambda^4}\right)(1 + \cos^2\theta_x) \quad \text{Eq. (9)}$$

2. Scatter Intensity Distribution

Figure 7B:
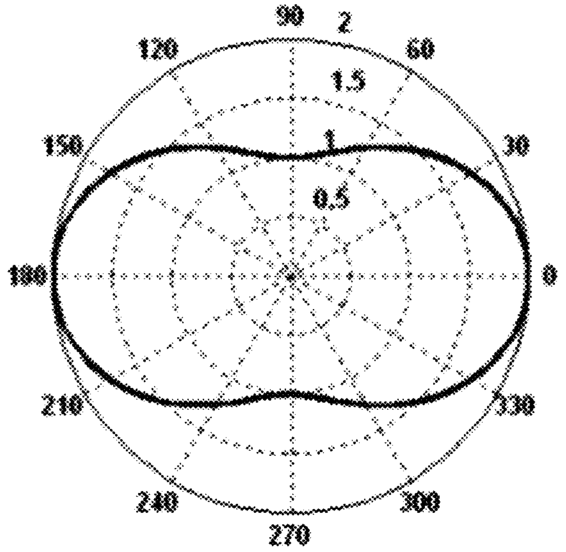
FIG. 7B is an illustration of scatter intensity distribution.

As illustrated in FIG. 7B, the scatter intensity is dependent on the number of particles, and the above equation is a function of $\theta_x$, the scatter angle. The maximum scatter angles are at 0 and 180.

For a given volume of observation, the scatter is superposition of many such distributions. For a sensor observing the scatter, the maximum intensity position, otherwise called a resultant intensity, is observed as a beam positioned at a location. Hence, particle size variations are captured as beam deflections.

C. Methods of Preparing Scatter Profiles

Typically, an aerosol is passed between the light irradiation part and the PD part or when a light irradiation part is passed across a stratified fluid on to a PD part. The location (i.e., the x and y positions) and preferably the power (also referred to intensity) of the scattered, incident light beam(s) are collected as analog data by the PD and converted to digital information by a DAQ part. In some embodiments, the original or default x and y positions and preferably the power of the light beam are also measured in the absence of an aerosol to determine the unscattered position and power of the light. In some embodiments, the unscattered position and power is pre-determined or otherwise previously known or preset.

The aerosol can be from a natural source, such as a subject's breath or cough, or an artificial source such as nebulizer or humidifier.

The measurements can be taken numerous times or repeatedly over a period of time and preferably in discrete and consistent intervals. This repetition in the measurement can be referred to as sampling and can be controlled by default settings in the PD part of user input provided thereto.

The measured data, also referred to as recorded data, is transferred or transmitted to a computer where it can be collected. A scatter algorithm can be applied to further characterize the particles and droplets of the aerosol. Additional information including, but not limited to, the deflection magnitude, the deflection direction, the deflection frequency, and size, sizes, or size range, density and rate or speed of particles and/or droplets in the aerosol, referred to as deduced data, can be determined from the recorded data. Some or all of the recorded or deduced data can be referred to as a profile for the aerosol or a profile of particular particles or droplets contained therein.

The experiments below tested various molarities of salt solution to illustrate these principles. It is possible to detect the particle size at different vapor speeds. Though the beam composition is a mix of all the properties in the medium, data processing can be used to investigate the particle sizes specifically even in a moving medium. The scattering data of the particles taken at different sampling times can provide the particle sizes (investigated in the salt experiments), and the deflection data of moving particles can provide the concentration, flow rate, and flow patterns in additional experiments.

In another exemplary proof of principle experiment, bacteria will be detected over at least 2 experiments, each spanning over 30 minutes in a controlled environment. Bacteria will be suspended in vapors and passed through the device and the beam data collected for the total duration. Two different bacteria types with distinguishable sizes and shapes will be used. The approximate data collected will be about 100 million data points for both the experiments.

In some embodiments, the method is used to prepare one or more profiles for a stratified fluid and/or an aerosol composed of particles and droplets of material(s). For example, in some embodiments, a nebulizer or humidifier, or a subject with a known disease or disorder, is used to deliver one or more aerosols, optionally in a stratified fluid, between the light irradiating part and the PD part. The particles and/or droplets can include microbes including, but not limited to, virus, bacterium, parasite, protozoan, fungus; environmental materials including, but not limited to, allergens and pollutants; and combinations thereof. Another example includes a medium of varying densities in any direction or a stratified fluid. In some embodiments, particles and droplets of material(s) or a stratified fluid having known contents are used to generate control profiles. In some embodiments, the contents of particles and droplets of material(s) or a stratified fluid are unknown. Test profiles can be prepared and compared to one or more control profiles to identify or determine one or more of the unknown contents.

D. Methods of Diagnosis, Prognosis, and Progression

Humans exhale particles of sizes between 0.3 μm to 100 μm diameter. For example, during coughing (0.5 μm to 40 μm), sneezing (2.0 μm to 16 μm), breathing (0.30 μm to 20 μm) (Bake, et al., *Respiratory research,* 20:8 (2019), doi: 10.1186/s12931-019-0970-9; Beasley, et al., *International journal of chronic obstructive pulmonary disease,* 7: 555-569 (2012), doi:10.2147/COPD.S28286), and talking. Both volatile and non-volatile compounds have been identified in exhaled breath condensate (EBC) i.e., exhaled water vapor that is condensed by the means of low temperature. See, e.g., U.S. Published Application No. 2010/00297635. The non-volatiles found in EBC are believed to originate from particles formed within the airways. These particles are generated in the respiratory system while breathing, speaking or coughing and are believed to serve as vehicles for transport of infectious material.

Measuring biomarkers in exhaled air is non-invasive and is conducive to repeated sampling which can be useful for early detection of disease as well as monitoring of disease progression and therapy response. Detection of diseases from exhaled breath has been shown in different fields of medicine (Nakhleh, et al., *ACS Nano,* 2017, 11, 112-125 DOI: 10.102 1/a csnano.6b04930), particularly infectiology (Phillips, Tuberculosis 2012, 92, 314-320; Phillips, et al., *Tuberculosis* 2010, 90, 145-151; Bean, et al., *Eur. Respir. J.* 2015, 45, 181-190;) respiratory medicine (Cohen-Kaminsky, et al., *Am. J. Respir. Crit. Care Med.* 2013, 188, 756-759; Allers, et al., *J. Breath Res.* 2016, 10, 026004; Baumbach, et al., *Int. J. Ion Mobility Spectrom.* 2011, 14, 159-166; Bos, et al., *Eur. Respir. J.* 2014, 44, 188-197; Mansoor, et al., *PLoS One* 2014, 9, e95331; Smith, et al., *J. Breath Res.* 2016, 10, 021002), and oncology (Haick, et al., *Chem. Soc. Rev.* 2014, 43, 1423-1449; Amann, et al., *J. Breath Res.* 2014, 8, 016003; Amann, et al., *Expert Rev. Mol. Diagn.* 2011, 11, 207-217; Phillips, et al., *Lancet* 1999, 353, 1930-1933; Zhang, et al., *Theranostics* 2014, 4, 154-162; Amal, et al., *Int. J. Cancer* 2016, 138, 229-236; Amal, et al., Gut 2016, 65, 400-407; Amal, *Int. J. Cancer* 2015, 136, E614—E622; Barash, et al., Nanomedicine (N. Y., NY, U. S.) 2012, 8, 580-589; Barash, et al., *Oncotarget* 2015, 6, 44864-44876; Davies, et al., *Br. J. Cancer* 2014, 111, 1213-1221; Hakim, et al., *Br. J. Cancer* 2011, 104, 1649-1655; Peled, et al., *J. Thorac. Oncol.* 2012, 7, 1528-1533; Peng, et al., *Br. J. Cancer* 2010, 103, 542-551; Peng, et al., *Nat. Nanotechnol.* 2009, 4, 669-673).

Thus, methods of diagnosis, prognosis, as well as monitoring disease progression and response to therapeutic interventions using the disclosed devices and systems are provided.

In some embodiments, identification of the contents of an unknown aerosol sample is used to assist in the diagnosis or prognosis of disease or disorder. In some embodiments, a scatter profile(s) including unknown material(s) is compared to one or more profiles of known material(s). If the scatter profile of an unknown material matches a scatter profile of a known material, the unknown material can be identified as the having the same, similar, or shared content with the known sample.

In some embodiments, a series of two or more different stratified fluid or aerosol samples from the same subject are delivered to the system. The two or more different samples can be administered minutes, hours, days, weeks, or months apart. Profiles prepared for the two or more different fluids or aerosols can be compared to each other or to control or known profiles. In some embodiments, the comparison includes identifying quantitative or qualitative differences in the two or more different scatter profiles. In such embodiments, the comparison may or may not further include a comparison to known profiles. Thus, in some embodiments, the methods are used to identify changes in a subject's scatter profile longitudinally. In such embodiments, the two or more different profiles can be used to monitor or otherwise evaluate disease or disorder progression in the subject, the effectiveness of an administered therapeutic treatment in the subject, determine when the subject is in need of a first or further administration of a therapeutic treatment, or the combination thereof. In such embodiments, the subject's disease or disorder may be known or may be unknown. In some embodiments, the subject may be administered a therapeutic treatment during this time (e.g., between delivery of the two different aerosols to the system). Additionally, or alternative, therapeutic treatment of a subject may be started or stopped after a certain scatter profile is achieved or identified. Improvement or deterioration of a disease or disorder can be measured by both subjective and objective methods, and can be quantified using a subjective scoring or a panel scoring, amongst other methods.

Any of the methods can include summarizing the aerosol's particle and droplet profile(s) into a clinical report that may or may not also include comparison of the profile(s) to known profiles, identification or characterization of the aerosol's particles and droplets (e.g., based on the comparison to known profile(s), or a combination thereof. For example, results can be summarized into a table of species found in the aerosol along with their relative proportion in the aerosol sample.

In some embodiments, the methods include detecting particles and classifying them based on optical scatter pattern optionally using machine-learning models based on several experiments. See e.g., Wan, *PloS one* 9(1):e87088 (2014), doi: 10.1371/journal.pone.0087088; Robinson, et al., *Optics and Photonics News,* 22(10):20-27 (2011); Fabian, et al., *Journal of aerosol medicine and pulmonary drug delivery,* 24(3):137-147 (2011); *Muir, Journal of applied physiology* 23(2):210-214 (1967); Xu, et al., *PloS one* 7(7):e41137 (2012), doi: 10.1371/journal-.pone.0041137. Any of the disclosed methods can further include calibration, data mining, and/or machine learning.

In some embodiments, the methods include providing the results, findings, diagnoses, predictions and/or treatment recommendations to the subject. For example, the results, findings, diagnoses, predictions and/or treatment recommendations can be recorded and communicated to technicians, physicians and/or patients or clients. In certain embodiments, computers will be used to communicate such information to interested parties, such as, clients, patients and/or the attending physicians.

In some embodiments, once a subject's aerosol is profiled or otherwise characterized, the profile or other characterization can be displayed and/or conveyed to a clinician, caregiver or a non-clinical provider, including the client/subject. For example, the results of the test can be provided to a user (such as a clinician or other health care worker, laboratory personnel, or patient) in a perceivable output that provides information about the results of the method. In some embodiments, the output is a paper output (for example, a written or printed output), a display on a screen, a graphical output (for example, a graph, chart, or other diagram), or an audible output.

In some embodiments, the output is a numerical value, such as an amount of one or more particular species or sets of particles or droplets in the test aerosol compared to a control. The output can be a graphical representation, for example, a graph that indicates the value (such as amount or relative amount) of the particular species of particle or droplet in the sample from the subject on a standard curve. In a particular example, the output (such as a graphical output) shows or provides a cut-off value or level that indicates the presence of a lung disease or disorder. In some examples, the output is communicated to the user, for example by providing an output via physical, audible, or electronic means.

The output can provide quantitative information (for example, an amount of one or more or all species of particles and/or droplets in a test aerosol sample compared to a control sample or value) or can provide qualitative information (e.g., absence or no detection, or mild, moderate, or severe presence of a respiratory disease or disorder). In additional examples, the output can provide qualitative information regarding the relative amount of one or more species of particles or droplets, such as identifying the presence of an increase relative to a control, a decrease relative to a control, or no change relative to a control.

In some embodiments, the output is accompanied by guidelines for interpreting the data, for example, numerical or other limits that indicate the presence or absence of a particular respiratory disease or disorder. The indicia in the output can, for example, include normal or abnormal ranges or a cutoff, which the recipient of the output may then use to interpret the results, for example, to arrive at a diagnosis, prognosis, susceptibility towards or treatment plan. In some examples, the findings are provided in a single page diagnostic report (e.g., PDF file) for the healthcare provider to use in clinical decision making.

Based on the findings, the therapy or protocol administered to a subject can be started, modified, not started, or re-started (in the case of monitoring for a reoccurrence of a particular condition/disorder). In some embodiments, recommendations of what treatment to provide are given either in verbal or written communication. In some embodiments, the recommendations are provided to the individual via a computer or in written format and accompany the diagnostic report. For example, a subject may request their diagnostic report and recommended treatment protocols be provided to them via electronic means. In some embodiments, the diagnostic report may include determination of other clinical or non-clinical information. In certain embodiments, the communication containing the diagnostic results and/or treatment recommendations or protocols based on the results, may be generated and delivered automatically to the subject using a combination of computer hardware and software.

In some embodiments, the treatment, dose or dosing regimen is modified based on the information obtained using the methods disclosed herein.

For example, a subject can be monitored while undergoing treatment using the methods described herein in order to assess the efficacy of the treatment or protocol. In this manner, the length of time or the amount of a treatment given to the subject can be modified based on the results obtained using the methods disclosed herein. The subject can also be monitored after the treatment using the methods described herein to monitor for relapse and thus, the effectiveness of the given treatment. In this manner, whether to resume treatment can be decided based on the results obtained using the methods disclosed herein. In some examples, this monitoring can be performed by a clinical healthcare provider. In other examples, this monitoring is performed by a non-clinical provider and can include self-monitoring or monitoring by a consultant.

Prognostic methods may include a visual representation of the test aerosol sample relative to other known samples of known outcome optionally along with statistically derived p-value values for provided data. Clinical outcome may be determined by analyzing statistically the probabilistic distance a test sample is from other samples of known outcomes and reporting such as a risk (e.g., risk of having or developing a diseases or disorder, or manifesting a certain symptom thereof such as an asthma attack).

In some embodiments, the system or analysis of collected data includes the ability to alert a subject to threat to the subject's health or wellness. For example, in some embodiments, the system can alert subjects of an anticipated Asthma attack and/or a deteriorating lung condition due to pneumonia or COPD. In some embodiments, the method further includes providing an appropriate therapy or protocol for the subject after reviewing the diagnostic and/or prognostic report. For example, a subject diagnosed with a particular disease or disorder can be provided a particular therapy. In some embodiments, the therapy includes administering an agent to alter one or more signs or symptoms associated with the identified disease or disorder. The treatment/protocol can be performed multiple times. For example, in some embodiments, the treatment is performed one, two, three, four, five, six, seven, or more times daily, weekly, monthly, or yearly.

The desired treatments or protocols may be administered via any means known to one of skill in the art. In particular embodiments, the administration is via an oral, enteral, or pulmonary route.

E. Diseases and Disorders

The disclosed systems and methods can be used to assist in the diagnosis, prognosis, treatment, and monitoring of a variety of diseases and disorders. Typically, the disease or disorder is a respiratory disease or disorder. The respiratory disease or disorder can be caused by an infection or can be a non-infectious condition. The disease or disorder can be acute or chronic disorder.

Exemplary respiratory diseases and disorders include, but are not limited to, acute bronchitis, acute respiratory distress syndrome (ARDS), alpha-1 antitrypsin deficiency, asbestosis, asthma, bronchiectasis, bronchiolitis, bronchiolitis obliterans with organizing pneumonia (BOOP), bronchopulmonary dysplasia, byssinosis, chronic bronchitis, chronic obstructive pulmonary disease (COPD), chronic thromboembolic pulmonary hypertension (CTEPH), coccidioidomycosis, cough, cryptogenic organizing pneumonia (COP), cystic fibrosis (CF), deep vein thrombosis (DVT)/blood clots, emphysema, hantavirus pulmonary syndrome (HPS), histoplasmosis, human metapneumovirus (hMPV), hypersensitivity pneumonitis, idiopathic pulmonary fibrosis (IPF), influenza (Flu), interstitial lung disease (ILD), lung cancer, lymphangioleiomyomatosis (LAM), mesothelioma, middle eastern respiratory syndrome (MERS), nontuberculosis mycobacteria (NTM), pertussis, pneumoconiosis, pneumonia, primary ciliary dyskinesia (PCD), pulmonary arterial hypertension (PAH), pulmonary fibrosis (PF), pulmonary hypertension, respiratory syncytial virus (RSV), sarcoidosis, severe acute respiratory syndrome (SARS), shortness of breath, silicosis, sleep apnea (OSA), sudden infant death syndrome (SIDS), and tuberculosis (TB).

In particular embodiments, the disease or disorder is, or includes, asthma, COPD, or pneumonia.

In some embodiments, the disease or disorder is caused by a human coronavirus. In some embodiments, the coronavirus is a common cold coronavirus such as 229E, NL63, 0C43, and HKU1. In some embodiments, the virus is a Severe acute respiratory syndrome-related virus, such as, SARSr-CoV BtKY72, SARS-CoV-2, SARSr-CoV RaTG13, SARS-CoV PC4-227, or SARS-CoV, preferably one that infects humans such as SARS-CoV or SARS-CoV-2. In some embodiments, the virus is a Middle East respiratory syndrome-related virus such as MERS-CoV.

In some embodiments, the disease or disorder is the common cold, SARS, MERS, or COVID-19.

The disclosed systems, methods, and strategies, can be further understood through the following numbered paragraphs.

1. A system for monitoring stratified fluids comprising:
   - a light irradiation part that emits light, a photo detector (PD) part comprising an active sensing area, and an analogue-to-digital conversion circuitry (DAQ Part)
   - wherein the light irradiation part and PD are aligned such that upon illumination the light can be propagated through a stratified fluid between the irradiation part and PD and received on the active sensing area of the PD part to generate an electrical signal;

wherein changes in the pattern of light received on the active sensing area and electrical signal generated therefrom correspond with changes comprising the amplitude and/or frequency of motion of and/or in the stratified fluid;

wherein the electrical signal is received by the DAQ part that converts the electrical signal to a digital signal, and optionally records the digital signal.

2. The system of paragraph 1, wherein the digital signal can be processed to determine the characteristics of the motion of one or more aerosols, and/or particles or droplets in the stratified fluid.
3. The system of paragraphs 1 or 2 wherein the digital signal can be used to detect and/or distinguish between one or more aerosols, and/or particles or droplets therein, of the stratified fluid.
4. The system of any one of paragraphs 1-3, wherein the digital signal can be processed in real time.
5. The system of any one of paragraphs 1-4, wherein the light irradiation part is a laser diode.
6. The system of any one of paragraphs 1-5, wherein the light is an un-collimated, un-processed raw point laser light beam.
7. The system of any one of paragraphs 1-6, wherein the light irradiation part is a low power diode laser operating in the visible region of the spectrum at 670 nm.
8. The system of paragraph 7, wherein the laser comprises a 5 mW power output.
9. The system of any one of paragraphs 1-8, wherein the PD is a solid state silicon photo detector.
10. The system of any one of paragraphs 1-9, wherein the active sensing area of the PD comprises a diameter of 10 mm.
11. The system of any one of paragraphs 1-10, wherein the active sensing area of the PD part comprises one or more photodiodes.
12. The system of any one of paragraphs 1-11, wherein the PD comprises an embedded BNC connector.
13. The system of any one of paragraphs 1-12 further comprising one or more amplifiers that can amplify the output electrical signal of the PD.
14. The system of any one of paragraphs 1-13, wherein the DAQ part comprises a computer bus that facilitates linkage between the DAQ part and a computer.
15. The system of any one of paragraphs 1-14, further comprising a voltage regulator.
16. The system of any one of paragraphs 1-15, further comprising a power supply.
17. The system of any one of paragraphs 1-16, further comprising a computer.
18. The system of any one of paragraphs 1-17, wherein the computer is selected from the group consisting of a supercomputer, mainframe computer, minicomputer, a microcomputer such as a desktop, or a mobile computer.
19. The system of paragraph 18, wherein the mobile computer is selected from the group consisting of a laptop, netbook, tablet, cellphone or smartphone.
20. The system of any one of paragraphs 1-19, further comprising a housing for one or more parts of the system.
21. The system of paragraph 20, wherein the housing contains or encloses a portion of, or all of, the light irradiation part, the PD part, the DAQ part, the voltage regulator, the power supply, or any combination thereof, optionally wherein the computer is not contained or enclosed in the housing.
22. The system of paragraph 21, wherein the part or parts arc contained or enclosed in one or more compartments in the housing.
23. The system of any one of paragraphs 20-22, wherein the housing further comprises one or more inlets and/or outlets to facilitate delivery of the aerosol into and/or through the housing.
24. The system of any one of paragraphs 20-23, wherein the housing comprises one or more channels or compartments for wires or connectors electrically connecting one or more of the parts.
25. The system of any one of paragraphs 20-24, wherein the housing comprises plastic.
26. The system of any one of paragraphs 20-25, wherein the housing is handheld.
27. The system of any one of paragraphs 17-26, wherein the computer processes the digital signal to determine the characteristics of the motion of and/or in the stratified fluid.
28. The system of paragraph 27, wherein processing the digital data comprises determining the deflection magnitude, the deflection direction, and/or the deflection frequency of the light; the size, sizes, or size range, density, and/or rate or speed of particles and/or droplets in the one or more aerosols; or any combination thereof.
29. The system of paragraphs 27 or 28, wherein the computer generates an output indicating the detection of and/or distinguishing between one or more aerosols, and/or particles or droplets therein, of the stratified fluid.
30. The system of any one of paragraphs 27-29, wherein the computer executes one or more algorithms, processes, and/or strategies disclosed herein to process the digital data.
31. The system of paragraph 30, wherein the algorithm, process, and/or strategy is based on the principles of Rayleigh scattering, scatter intensity distribution, or a combination thereof.
32. A housing according to any one of paragraphs 20-26.
33. A device comprising a light irradiation part, a PD part, a DAQ part, a voltage regulator, a power supply, or any combination thereof partially or completely contained or enclosed in the housing of paragraph 32.
34. The device of paragraph 33 in wired or wireless connectivity with a computer, preferably wherein the device docs not comprise the computer.
35. A method of characterizing an aerosol and/or particles and/or droplets thereof comprising passing an effective amount light irradiated by the light irradiation part of the system of any one of paragraphs 1-31 or the device of paragraphs 33 or 34 through the aerosol or a stratified fluid comprising the aerosol for the PD part to detect light scattered by the aerosol.
36. The method of paragraph 34, wherein the aerosol or stratified fluid comprising the aerosol is delivered to the system by a subject breathing and/or coughing into the system.
37. The method of paragraph 36, wherein the subject has, or is suspected of having, a respiratory disease or disorder.
38. The method of any one of paragraphs 34-37 further comprising recording, collecting and/or processing the digital data by the system, on a computer linked thereto, or a combination thereof.

39. The method of any one of paragraphs 34-38 comprising repeating the detecting, generating, converting, and optionally the recording, collecting and/or processing one or more times, optionally for a fixed period(s) and/or optionally at a fixed time interval(s).
40. The method of any one of paragraphs 35-39, wherein the processing comprises using the digital data to determine the deflection magnitude, the deflection direction, and/or the deflection frequency of the light; the size, sizes, or size range, density, and/or rate or speed of particles and/or droplets in one or more aerosols; or any combination thereof.
41. The method of any one of paragraphs 35-40, wherein the stratified fluid and/or aerosol comprises particles and/droplets of unknown content.
42. The method of any one of paragraphs 35-41, wherein the stratified fluid is delivered to the system by a subject, the stratified fluid comprises one or more aerosols characteristic of a respiratory disease or disorder, and the system identifies the disease or disorder by processing the characteristics of the aerosol and matching them to aerosol characteristics of the disease or disorder.
43. An aerosol profile comprising the x and/or y position, the power, the deflection magnitude, the deflection direction, and/or the deflection frequency of the scattered light; the size, sizes, or size range, density, and/or rate or speed of particles and/or droplets in the aerosol; or any combination thereof, prepared according to the method of any one of paragraphs 35-42.
44. A method of diagnosing a respiratory disease or disorder of a subject comprising comparing one or more aerosol profiles of paragraph 43 of the subject with one or more disease or disorder aerosol profiles, and diagnosing the subject as having a disease or disorder or when one or more of the subject's aerosol profiles matches one or more aerosol profiles of the corresponding disease or disorder.
45. A method of determining the effectiveness of a treatment comprising comparing first and second aerosol profiles according to paragraph 43 of a subject with a disease or disorder to a healthy aerosol profile, wherein the first and second aerosol profiles are prepared before and after at least one treatment for the disease or disorder respectively, and wherein the treatment is determined to be effective if the subject's second aerosol profile is more similar to the healthy profile than the first profile.
46. The method of paragraphs 44 or 45, wherein the respiratory disease or disorder is asthma, pneumonia, or Chronic Obstructive Pulmonary Disease (COPD).
47. A system or device according a figure and/or its description as provided herein.

EXAMPLES

Example 1: Aerosols can be Characterized by Photo Detection of Scattered Laser Light Materials and Methods Scatter System A diode laser of 670 nm was collimated through a pinhole and pointed on to a photo detector (PD) in a forward scatter configuration ($\theta_x$=180°) as shown in FIG. 1. The 670 nm used was connected to a 3V and 1.2 amp external DC source power adapter. The Photo Detector used was OBP-U-9H (NewPort) with an active sensing area of dimensions 9×9 mm and measured beam displacement with positional accuracy of +/−15 μm and optical power between 1 μW to 250 μW. The PD comes with an external DAQ with a peak sampling rate of 30 kHz. The PD detected beam positions of wavelengths between 300 nm and 1100 nm with a peak responsivity at 990 nm. The sensor-DAQ system was connected to a desktop computer through a USB connector. Data was recorded using OBP-Software-2.03. The software recorded beam position along x and y axis and power at 16 Hz in .csv (comma separated value) format. The recorded data was analyzed using Matlab software.

Particle Simulation

Figure 2A:
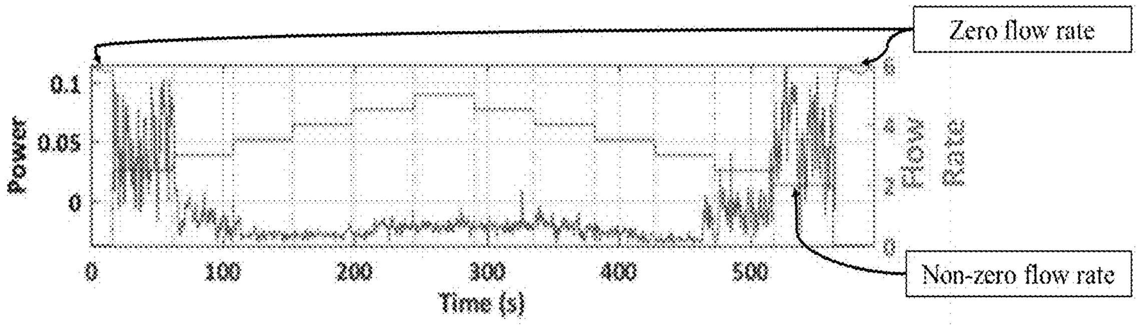
FIGS. 2A-2C are plots of the change in beam power over time (FIG. 2A), average beam power over different flow rate windows (FIG. 2B) and the result of bagged trees mapping function applied on beam power data (FIG. 2C). Each plot includes an overlay of the particle flow rate (right Y-axis) supplied to the diffuser in 14 time intervals.

In order to simulate the breathing process, a hand held nebulizer (Uniclife) was used to induce particles into an air stream. A distilled water spray and the stream from nebulizer was blown across the laser and sensor section as shown in FIG. 1 and FIG. 5C. The hand held nebulizer circuit was modified to connect an Arduino device. The nebulizer particle rate was controlled through the Arduino device programmed to run at 8 different speeds as illustrated in FIG. 2A.

Assay

An experiment was carried out, starting at zero diffusion rates on the nebulizer. The rates were changed at a rate of 10% of the maximum delivery rate of the nebulizer starting from 50%. Each flow rate was maintained for 60 s. After the peak flow rate (100%) was achieved, the rate was dropped at the same 10% rate until a minimum of 40% of the maximum flow rate and finally dropped to zero.

During this process, the beam passing across the nebulizer output was recorded from the PD— DAQ system.

Results

Figure 2B:
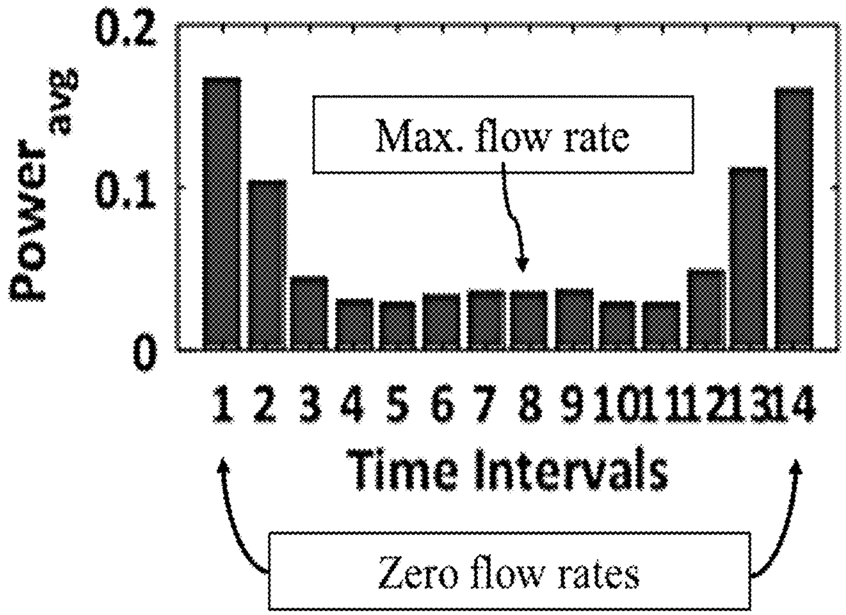

The raw data recorded in the experiment for beam power is shown in FIG. 2A and an overlay of the flow rate (horizontal steps) is also presented. Variation in power can be clearly distinguished during the presence and absence of aerosol particles in the raw data. FIG. 2B presents results of moving average applied on power data, averaged over each flow rate interval. A clear step distinction in the power and beam position with change in flow rates can be observed.

Mapping Function

Figure 2C:
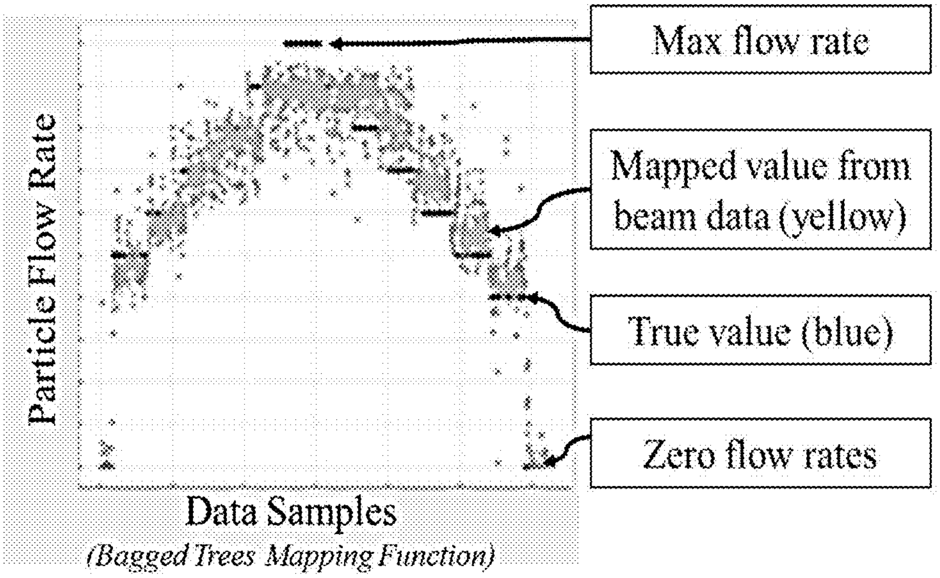

For the acquired data, the performance of linear regression, linear and quadratic SVMs (Support Vector Machines), Fine Gaussian SVM, Boosted Trees and Bagged Trees was analyzed. The analysis showed best fit (lowest MSE) for Bagged Trees. The results from bagged trees mapping function and the validation result between beam power to flow rate is presented in FIG. 2C.

Example 2: A Prototype Device Can Distinguish Aerosols Generated From Varying Salt Concentration Solutions Mimicking Biomarkers of Varying Densities/Compositions Materials and Methods Scatter System A housing for holding components of the system, including a laser and PD, was designed using CAD modeling and 3D printed from a clear resin. The housing included enclosures for accommodating the electronics for detecting the aerosol particle density. All the parts were assembled for testing. See, e.g., FIGS. 5A-5C.

A portable, hand-holdable device including a laser and PD within the housing was assembled. Sec FIGS. 4 and 5D, which illustrate system set-ups including the device. A pipe-like provision was included for blowing through the device. The device can be used to directly blow through or connect it to extended piping for a breathing mask (as illustrated in FIG. 5D). The PD used was QP50-6SD2 and a 670 nm diode laser similar to the one used in example 1 was used.

Particle Simulation

In order to simulate the breathing process, a hand held nebulizer (Uniclife) was used to induce particles into an air stream. The stream from nebulizer was blown across the laser and sensor section as shown in FIG. 1 and FIG. 5C. The hand held nebulizer circuit was modified to connect an Arduino device. The nebulizer particle rate was controlled through the Arduino device programmed to run at 8 different speeds as illustrated in FIG. 2A.

Assay

An experiment similar to the one described in Example 1 was conducted. An outline of the configuration is presented in FIGS. 4 and 5D. In addition to the experiment sequence in Example 1, a salt concentrate solution was used instead of distilled water for the generation of aerosol particles. Pure NaCl, crystals were used for making salt solutions of molarities 0.1, 0.5, 1, and 10. Multiple trials with different salt solutions were conducted starting at zero rates and increasing in steps at 10% of maximum flow rate of nebulizer starting at 50% until 100% (Max.) flow rate for about 300 seconds. Beam power data for each trial was recorded and plotted as shown in FIGS. 3A and 3B.

Results

Figure 3A:
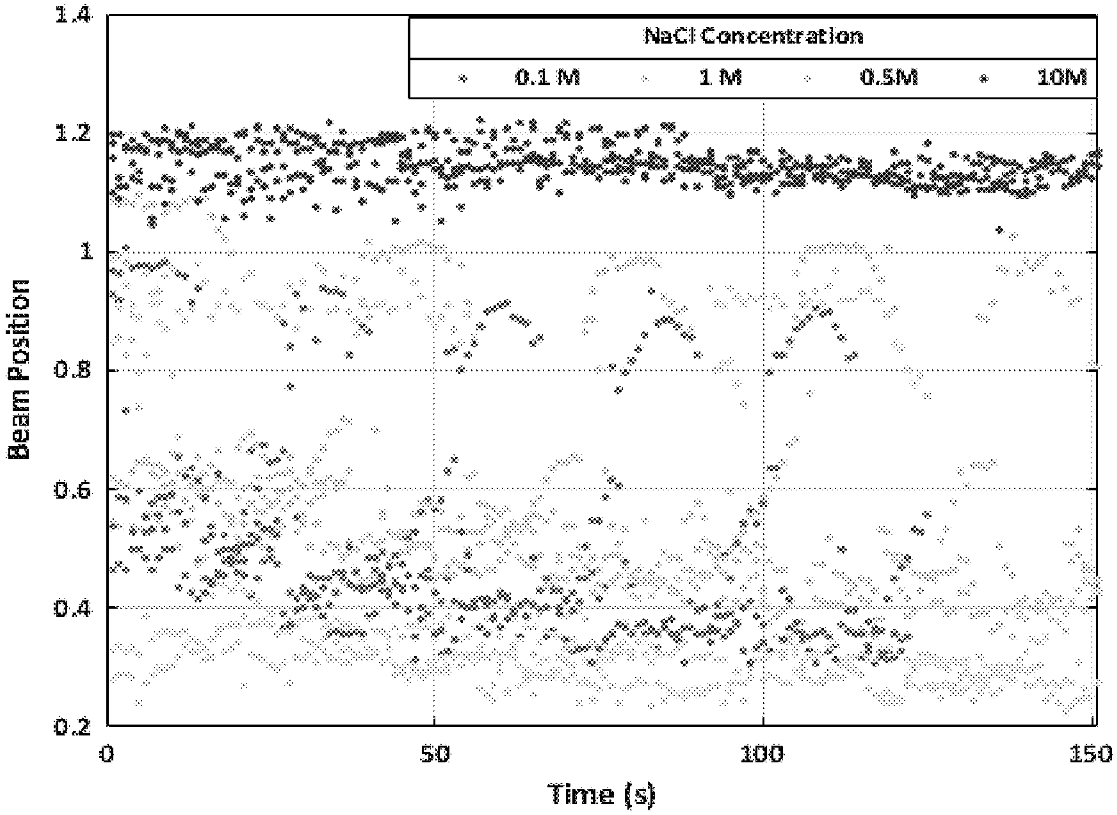
FIGS. 3A and 3B are plots showing variation in power values (beam position) of the scattered beam passed across aerosol particles generated from salt solutions of different molarities over 150 seconds (FIG. 3A) and 300 seconds (FIG. 3B).
Figure 3B:
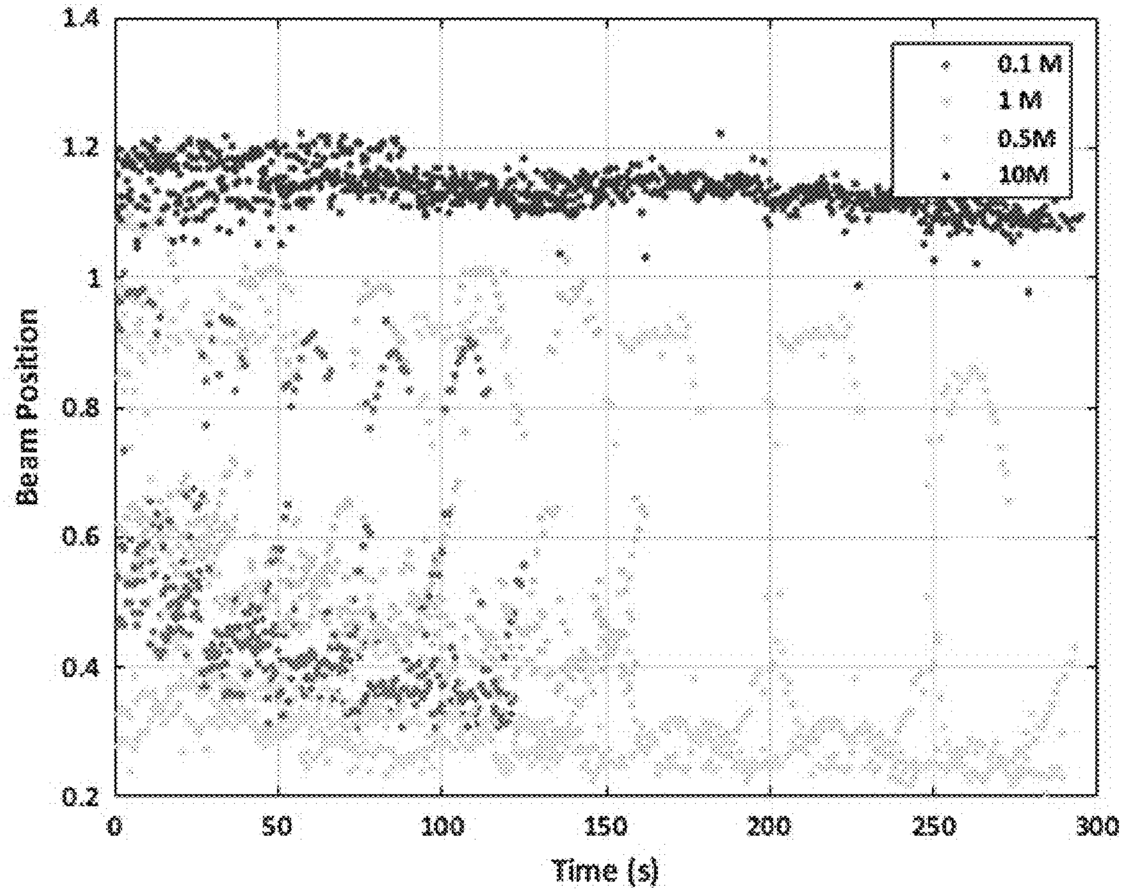

The raw data recorded in the experiment for beam power over various trials is shown in FIGS. 3A and 3B. In each trial, a different molarity of solution was used for aerosol generation from the nebulizer. The molaritics used were 0.1, 0.5, 1 and 10, with three trials for each salt concentration. The coloring of the points is based on the molarity. A clear distinction was observed in the beam power for different molarities. A clear band gap can be observed in the point scatter cloud distinguishing different molarities assimilating varying particle sizes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A system for monitoring stratified fluids comprising:

a single light irradiation part that emits light, a single photo detector (PD) part comprising an active sensing area, and an analogue-to-digital conversion circuitry (DAQ Part), wherein the light irradiation part and PD are aligned such that upon illumination the light is propagated through a stratified fluid between the irradiation part and PD and received as forward scattered light on the active sensing area of the PD part to generate an electrical signal;

wherein changes in the pattern of forward scattered light received on the active sensing area and electrical signal generated therefrom correspond with changes comprising the amplitude and/or frequency of motion of and/or in the stratified fluid;

wherein the electrical signal is received by the DAQ part that converts the electrical signal to a digital signal, and optionally records the digital signal.

2. The system of claim 1, wherein the light irradiation part is a laser diode, and the light is an un-collimated, unprocessed raw point laser light beam, the PD is a solid-state silicon photo detector, or a combination thereof.

3. The system of claim 2, further comprising a computer.

4. The system of claim 3, wherein the computer processes the digital signal to determine the characteristics of the motion of one or more aerosols and/or particles or droplets in the stratified fluid.

5. The system of claim 4, wherein processing the digital signal comprises determining the deflection magnitude, the deflection direction, and/or the deflection frequency of the light; the size, sizes, or size range, density, and/or rate or speed of one or more aerosols and/or particles and/or droplets in the stratified fluid or any combination thereof.

6. The system of claim 5, wherein the computer executes one or more algorithms, processes, and/or strategies based on the principles of Rayleigh scattering, scatter intensity distribution, or a combination thereof to process the digital signal.

7. The system of claim 6, wherein the computer generates an output indicating the detection of and/or distinguishing between, one or more aerosols and/or particles or droplets therein, of the stratified fluid.

8. The system of claim 7, further comprising a voltage regulator, a power supply, and a housing, wherein the housing comprises one or more inlets and/or outlets to facilitate delivery of the aerosol into and/or through the housing and contains or encloses at least a portion of the light irradiation part, the PD part, the DAQ part, the voltage regulator, the power supply, or any combination thereof.

9. The system of claim 8, wherein the housing is handheld.

10. The system of claim 9, wherein the light irradiation part, the PD part, the DAQ part, the voltage regulator, and the power supply are contained or enclosed in the housing, wherein the computer is not contained or enclosed in the housing, and wherein the computer is in wireless connection with one or more parts in the housing.

11. A method of characterizing one or more aerosols and/or particles and/or droplets comprising passing an effective amount of light irradiated by the light irradiation part of the system of claim 1 through a stratified fluid comprising the aerosol and detecting forward scattered light scattered by the particles and/or droplets using the PD part.

12. The method of claim 11, comprising a subject breathing or coughing to deliver the stratified fluid into the system.

13. The method of claim 12, wherein the subject has, or is suspected of having, a respiratory disease or disorder.

14. The method of claim 13 further comprising recording, collecting and/or processing the digital signal by a computer linked to the system.

15. The method of claim 14 comprising repeating the detecting, generating, converting, and optionally the recording, collecting and/or processing one or more times, optionally for a fixed period(s) and/or optionally at a fixed time interval(s).

16. The method of claim 15, wherein the processing comprises using the digital signal to determine the deflection magnitude, the deflection direction, and/or the deflection frequency of the light; the size, sizes, or size range, density, and/or rate or speed of particles and/or droplets in the stratified fluid; or any combination thereof.

17. The method of claim 16, wherein the computer executes one or more algorithms, processes, and/or strategies based on the principles of Rayleigh scattering, scatter intensity distribution, or a combination thereof to process the digital signal.

18. The method of claim 17, wherein the stratified fluid and/or aerosol comprises particles and/droplets of unknown content.

19. A method of diagnosing a respiratory disease or disorder of a subject comprising comparing one or more aerosol profiles of the subject comprising x and/or y position, the power, the deflection magnitude, the deflection direction, and/or the deflection frequency of the scattered light; the size, sizes, or size range, density, and/or rate or speed of particles and/or droplets in the aerosol; or any combination thereof, prepared according to the method of claim 12 with one or more known disease or disorder aerosol profiles, and diagnosing the subject as having a disease or disorder or when one or more of the subject's aerosol profiles matches one or more aerosol profiles of the corresponding disease or disorder.

20. A method of determining the effectiveness of a treatment of subject for a disease or disorder comprising comparing first and second aerosol profiles of the subject comprising x and/or y position, the power, the deflection magnitude, the deflection direction, and/or the deflection frequency of the scattered light; the size, sizes, or size range, density, and/or rate or speed of particles and/or droplets in the aerosol; or any combination thereof, prepared according to the method of claim 12 to a healthy aerosol profile, wherein the first and second aerosol profiles are prepared before and after at least one treatment for the disease or disorder respectively, and wherein the treatment is determined to be effective if the subject's second aerosol profile is more similar to the healthy profile than the first profile.

21. The system of claim 1, wherein the alignment angle between light irradiated from the light irradiation part and the active sensing area of the PD part is 180 degrees.

22. A system for monitoring stratified fluids comprising:

a laser diode that emits an un-collimated, un-processed raw point laser light beam, a photo detector (PD) part comprising an active sensing area, an analogue-to-digital conversion circuitry (DAQ Part), a voltage regulator, a power supply, a handheld housing comprising one or more inlets and/or outlets to facilitate delivery of a stratified fluid into and/or through the housing and at least a portion of the laser diode, the PD part, the DAQ part, the voltage regulator, the power supply, or any combination thereof contained or enclosed therein, and a computer not contained or enclosed in the housing that is in wireless connection with one or more parts in the housing;

wherein the laser diode and PD are aligned such that upon illumination the light is propagated through a stratified fluid between the irradiation part and PD and received on the active sensing area of the PD part to generate an electrical signal;

wherein changes in the pattern of light received on the active sensing area and electrical signal generated therefrom correspond with changes comprising the amplitude and/or frequency of motion of and/or in the stratified fluid;

wherein the electrical signal is received by the DAQ part that converts the electrical signal to a digital signal, and wherein the computer processes the digital signal to determine the characteristics of the motion of one or more aerosols and/or particles or droplets in the stratified fluid by determining the deflection magnitude, the deflection direction, and/or the deflection frequency of the light; the size, sizes, or size range, density, and/or rate or speed of particles and/or droplets in the one or more aerosols; or any combination thereof using one or more algorithms, processes, and/or strategies based on the principles of Rayleigh scattering, scatter intensity distribution, or a combination thereof to process the digital signal, and generates an output indicating the detection of and/or distinguishing between, one or more aerosols and/or particles or droplets therein, of the stratified fluid.

* * * * *

UNITED STATES PATENT AND TRADEMARK OFFICE
CERTIFICATE OF CORRECTION

| | | |
|---|---|---|
| PATENT NO. | : 11,957,447 B2 | Page 1 of 1 |
| APPLICATION NO. | : 16/905480 | |
| DATED | : April 16, 2024 | |
| INVENTOR(S) | : Tatavarti et al. | |

It is certified that error appears in the above-identified patent and that said Letters Patent is hereby corrected as shown below:

In the Specification

Column 1, Lines 15-18, replace the following paragraph:
"This invention was made with government support under grant numbers GM104528 and HHSN272201400008C awarded by the NIH and 1150042 and 1659525 awarded by the NSF. The Government has certain rights in the invention."

With the following paragraph:
--This invention was made with government support under HHSN272201400008C, and GM104528 awarded by the National Institutes of Health, and 1150042, and 1659525 awarded by the National Science Foundation. The government has certain rights in the invention.--

Signed and Sealed this
Twelfth Day of November, 2024

Katherine Kelly Vidal
*Director of the United States Patent and Trademark Office*